US012327623B2

(12) United States Patent
Guaneri et al.

(10) Patent No.: US 12,327,623 B2
(45) Date of Patent: Jun. 10, 2025

(54) SYSTEM AND METHOD FOR PROCESSING MEDICAL CLAIMS

(71) Applicant: ROM TECHNOLOGIES, INC., Brookfield, CT (US)

(72) Inventors: Joseph Guaneri, Brookfield, CT (US); Daniel Posnack, Brookfield, CT (US); Peter Arn, Brookfield, CT (US); Wendy Para, Brookfield, CT (US); S. Adam Hacking, Brookfield, CT (US); Micheal Mueller, Brookfield, CT (US); Jonathan Greene, Brookfield, CT (US); Steven Mason, Brookfield, CT (US)

(73) Assignee: ROM Technologies, Inc., Brookfield, CT (US)

( * ) Notice: Subject to any disclaimer, the term of this patent is extended or adjusted under 35 U.S.C. 154(b) by 1055 days.

(21) Appl. No.: 17/147,642

(22) Filed: Jan. 13, 2021

(65) Prior Publication Data
US 2021/0142893 A1 May 13, 2021

Related U.S. Application Data

(63) Continuation-in-part of application No. 17/021,895, filed on Sep. 15, 2020, now Pat. No. 11,071,597.
(Continued)

(51) Int. Cl.
*G16H 20/30* (2018.01)
*A63B 24/00* (2006.01)
(Continued)

(52) U.S. Cl.
CPC ......... *G16H 20/30* (2018.01); *A63B 24/0062* (2013.01); *G06Q 10/10* (2013.01);
(Continued)

(58) Field of Classification Search
CPC ..... G16H 10/00–80/00; A63B 24/0062; A63B 2225/10; G06Q 10/10; G06Q 40/08
See application file for complete search history.

(56) References Cited

U.S. PATENT DOCUMENTS

| 59,915 | A | 11/1866 | Lallement |
| 363,522 | A | 5/1887 | Knous |

(Continued)

FOREIGN PATENT DOCUMENTS

| CA | 2698078 A1 | 3/2010 |
| CA | 3193419 A1 | 3/2022 |

(Continued)

OTHER PUBLICATIONS

Huang et al., "ISO/IEEE 11073 Treadmill Interoperability Framework and its Test Method: Design and Implementation," JMIR Med Inform. Dec. 2020; 8(12): e22000. Published online Dec. 9, 2020. doi: 10.2196/22000: 10.2196/22000. (Year: 2020).*

(Continued)

*Primary Examiner* — Jonathon A. Szumny
(74) *Attorney, Agent, or Firm* — Dickinson Wright PLLC; Jonathan H. Harder; Stephen A. Mason

(57) ABSTRACT

A computer-implemented system for processing medical claims is disclosed. The system includes a medical device configured to be manipulated by a user while the user performs a treatment plan; a patient interface associated with the medical device, the patient interface comprising an output configured to present telemedicine information associated with a telemedicine session; and a processor. During the telemedicine session, the processor is configured to receive information from a medical device. Using the device-generated information, the processor is further configured to determine device-based medical coding information. The processor is further configured to transmit the
(Continued)

device-based medical coding information to a claim adjudication server.

26 Claims, 11 Drawing Sheets

Related U.S. Application Data

(60) Provisional application No. 63/028,392, filed on May 21, 2020, provisional application No. 62/910,232, filed on Oct. 3, 2019.

(51) Int. Cl.
| | |
|---|---|
| *G06Q 10/10* | (2023.01) |
| *G06Q 40/08* | (2012.01) |
| *G16H 10/60* | (2018.01) |
| *G16H 40/20* | (2018.01) |
| *G16H 40/67* | (2018.01) |
| *G16H 50/70* | (2018.01) |
| *G16H 70/20* | (2018.01) |

(52) U.S. Cl.
CPC ............ *G16H 10/60* (2018.01); *G16H 40/20* (2018.01); *G16H 40/67* (2018.01); *G16H 50/70* (2018.01); *G16H 70/20* (2018.01); *A63B 2225/20* (2013.01); *G06Q 40/08* (2013.01)

(56) References Cited

U.S. PATENT DOCUMENTS

| | | | |
|---|---|---|---|
| 446,671 A | 2/1891 | Elliott |
| 610,157 A | 8/1898 | Campbell |
| 631,276 A | 8/1899 | Bulova |
| 823,712 A | 6/1906 | Uhlmann |
| 1,149,029 A | 8/1915 | Clark |
| 1,227,743 A | 5/1917 | Burgedorfp |
| 1,784,230 A | 12/1930 | Freeman |
| 3,081,645 A | 3/1963 | Bergfors |
| 3,100,640 A | 8/1963 | Weitzel |
| 3,137,014 A | 6/1964 | Meucci |
| 3,143,316 A | 8/1964 | Shapiro |
| 3,713,438 A | 1/1973 | Knutsen |
| 3,744,480 A | 7/1973 | Gause et al. |
| 3,888,136 A | 6/1975 | Lapeyre |
| 4,079,957 A | 3/1978 | Blease |
| 4,408,613 A | 10/1983 | Relyea |
| 4,436,097 A | 3/1984 | Cunningham |
| 4,446,753 A | 5/1984 | Nagano |
| 4,477,072 A | 10/1984 | DeCloux |
| 4,499,900 A | 2/1985 | Petrofsky et al. |
| 4,509,742 A | 4/1985 | Cones |
| 4,606,241 A | 8/1986 | Fredriksson |
| 4,611,807 A | 9/1986 | Castillo |
| 4,616,823 A | 10/1986 | Yang |
| 4,648,287 A | 3/1987 | Preskitt |
| 4,673,178 A | 6/1987 | Dwight |
| 4,822,032 A | 4/1989 | Whitmore et al. |
| 4,824,104 A | 4/1989 | Bloch |
| 4,850,245 A | 7/1989 | Feamster et al. |
| 4,858,942 A | 8/1989 | Rodriguez |
| 4,860,763 A | 8/1989 | Schminke |
| 4,869,497 A | 9/1989 | Stewart et al. |
| 4,915,374 A | 4/1990 | Watkins |
| 4,930,768 A | 6/1990 | Lapcevic |
| 4,932,650 A | 6/1990 | Bingham et al. |
| 4,961,570 A | 10/1990 | Chang |
| 5,137,501 A | 8/1992 | Mertesdorf |
| 5,161,430 A | 11/1992 | Febey |
| 5,202,794 A | 4/1993 | Schnee et al. |
| 5,240,417 A | 8/1993 | Smithson et al. |
| 5,247,853 A | 9/1993 | Dalebout |
| 5,256,117 A | 10/1993 | Potts et al. |
| 5,282,748 A | 2/1994 | Little |
| 5,284,131 A | 2/1994 | Gray |
| 5,316,532 A | 5/1994 | Butler |
| 5,318,487 A | 6/1994 | Golen |
| 5,324,241 A | 6/1994 | Artigues et al. |
| 5,336,147 A | 8/1994 | Sweeney, III |
| 5,338,272 A | 8/1994 | Sweeney, III |
| 5,356,356 A | 10/1994 | Hildebrandt |
| 5,361,649 A | 11/1994 | Slocum, Jr. |
| D359,777 S | 6/1995 | Hildebrandt |
| 5,429,140 A | 7/1995 | Burdea et al. |
| 5,458,022 A | 10/1995 | Mattfeld et al. |
| 5,487,713 A | 1/1996 | Butler |
| 5,566,589 A | 10/1996 | Buck |
| 5,580,338 A | 12/1996 | Scelta et al. |
| 5,676,349 A | 10/1997 | Wilson |
| 5,685,804 A | 11/1997 | Whan-Tong et al. |
| 5,738,636 A | 4/1998 | Saringer et al. |
| 5,860,941 A | 1/1999 | Saringer et al. |
| 5,950,813 A | 9/1999 | Hoskins et al. |
| 6,007,459 A | 12/1999 | Burgess |
| D421,075 S | 2/2000 | Hildebrandt |
| 6,053,847 A | 4/2000 | Stearns et al. |
| 6,077,201 A | 6/2000 | Cheng |
| 6,102,834 A | 8/2000 | Chen |
| 6,110,130 A | 8/2000 | Kramer |
| 6,155,958 A | 12/2000 | Goldberg |
| 6,162,189 A | 12/2000 | Girone et al. |
| 6,182,029 B1 | 1/2001 | Friedman |
| 6,253,638 B1 | 7/2001 | Bermudez |
| 6,267,735 B1 | 7/2001 | Blanchard et al. |
| 6,273,863 B1 | 8/2001 | Avni et al. |
| 6,371,891 B1 | 4/2002 | Speas |
| 6,413,190 B1 | 7/2002 | Wood et al. |
| 6,430,436 B1 | 8/2002 | Richter |
| 6,436,058 B1 | 8/2002 | Krahner et al. |
| 6,450,923 B1 | 9/2002 | Vatti |
| 6,474,193 B1 | 11/2002 | Farney |
| 6,491,649 B1 | 12/2002 | Ombrellaro |
| 6,514,085 B2 | 2/2003 | Slattery et al. |
| 6,535,861 B1 | 3/2003 | OConnor et al. |
| 6,543,309 B2 | 4/2003 | Heim |
| 6,589,139 B1 | 7/2003 | Butterworth |
| 6,601,016 B1 | 7/2003 | Brown et al. |
| 6,602,191 B2 | 8/2003 | Quy |
| 6,613,000 B1 | 9/2003 | Reinkensmeyer et al. |
| 6,626,800 B1 | 9/2003 | Casler |
| 6,626,805 B1 | 9/2003 | Lightbody |
| 6,640,122 B2 | 10/2003 | Manoli |
| 6,640,662 B1 | 11/2003 | Baxter |
| 6,652,425 B1 | 11/2003 | Martin et al. |
| 6,662,168 B1 * | 12/2003 | Wallach ............... G06N 20/00 |
| | | 706/14 |
| 6,820,517 B1 | 11/2004 | Farney |
| 6,865,969 B2 | 3/2005 | Stevens |
| 6,890,312 B1 | 5/2005 | Priester et al. |
| 6,895,834 B1 | 5/2005 | Baatz |
| 6,902,513 B1 | 6/2005 | McClure |
| 7,058,453 B2 | 6/2006 | Nelson et al. |
| 7,063,643 B2 | 6/2006 | Arai |
| 7,156,665 B1 | 1/2007 | OConnor et al. |
| 7,156,780 B1 | 1/2007 | Fuchs et al. |
| 7,169,085 B1 | 1/2007 | Killin et al. |
| 7,204,788 B2 | 4/2007 | Andrews |
| 7,209,886 B2 | 4/2007 | Kimmel |
| 7,226,394 B2 | 6/2007 | Johnson |
| RE39,904 E | 10/2007 | Lee |
| 7,507,188 B2 | 3/2009 | Nurre |
| 7,594,879 B2 | 9/2009 | Johnson |
| 7,610,192 B1 * | 10/2009 | Jamieson ............... G06F 40/131 |
| | | 705/2 |
| 7,628,730 B1 | 12/2009 | Watterson et al. |
| D610,635 S | 2/2010 | Hildebrandt |
| 7,778,851 B2 | 8/2010 | Schoenberg et al. |
| 7,809,601 B2 | 10/2010 | Shaya et al. |
| 7,815,551 B2 | 10/2010 | Merli |
| 7,833,135 B2 | 11/2010 | Radow et al. |
| 7,837,472 B1 | 11/2010 | Elsmore et al. |
| 7,955,219 B2 | 6/2011 | Birrell et al. |
| 7,969,315 B1 | 6/2011 | Ross et al. |

(56) References Cited

U.S. PATENT DOCUMENTS

| | | |
|---|---|---|
| 7,974,689 B2 | 7/2011 | Volpe et al. |
| 7,988,599 B2 | 8/2011 | Ainsworth et al. |
| 8,012,107 B2 | 9/2011 | Einav et al. |
| 8,021,270 B2 | 9/2011 | D'Eredita |
| 8,038,578 B2 | 10/2011 | Olrik et al. |
| 8,079,937 B2 | 12/2011 | Bedell |
| 8,113,991 B2 | 2/2012 | Kutliroff |
| 8,172,724 B2 | 5/2012 | Solomon |
| 8,177,732 B2 | 5/2012 | Einav et al. |
| 8,287,434 B2 | 10/2012 | Zavadsky et al. |
| 8,298,123 B2 | 10/2012 | Hickman |
| 8,371,990 B2 | 2/2013 | Shea |
| 8,419,593 B2 | 4/2013 | Ainsworth et al. |
| 8,465,398 B2 | 6/2013 | Lee et al. |
| 8,506,458 B2 | 8/2013 | Dugan |
| 8,515,777 B1 | 8/2013 | Rajasenan |
| 8,540,515 B2 | 9/2013 | Williams et al. |
| 8,540,516 B2 | 9/2013 | Williams et al. |
| 8,556,778 B1 | 10/2013 | Dugan |
| 8,607,465 B1 | 12/2013 | Edwards |
| 8,613,689 B2 | 12/2013 | Dyer et al. |
| 8,615,529 B2 | 12/2013 | Reiner |
| 8,672,812 B2 | 3/2014 | Dugan |
| 8,751,264 B2 | 6/2014 | Beraja et al. |
| 8,784,273 B2 | 7/2014 | Dugan |
| 8,818,496 B2 | 8/2014 | Dziubinski et al. |
| 8,823,448 B1 | 9/2014 | Shen |
| 8,845,493 B2 | 9/2014 | Watterson et al. |
| 8,849,681 B2 | 9/2014 | Hargrove et al. |
| 8,864,628 B2 | 10/2014 | Boyette et al. |
| 8,893,287 B2 | 11/2014 | Gjonej et al. |
| 8,911,327 B1 | 12/2014 | Boyette |
| 8,979,711 B2 | 3/2015 | Dugan |
| 9,004,598 B2 | 4/2015 | Weber |
| 9,167,281 B2 | 10/2015 | Petrov et al. |
| 9,248,071 B1 | 2/2016 | Brenda |
| 9,272,185 B2 | 3/2016 | Dugan |
| 9,283,434 B1 | 3/2016 | Wu |
| 9,295,878 B2 | 3/2016 | Corbalis et al. |
| 9,311,789 B1 | 4/2016 | Gwin |
| 9,367,668 B2 | 6/2016 | Flynt et al. |
| 9,409,054 B2 | 8/2016 | Dugan |
| 9,443,205 B2 | 9/2016 | Wall |
| 9,474,935 B2 | 10/2016 | Abbondanza et al. |
| 9,480,873 B2 | 11/2016 | Chuang |
| 9,481,428 B2 | 11/2016 | Gros |
| 9,514,277 B2 | 12/2016 | Hassing et al. |
| 9,566,472 B2 | 2/2017 | Dugan |
| 9,579,056 B2 | 2/2017 | Rosenbek et al. |
| 9,629,558 B2 | 4/2017 | Yuen et al. |
| 9,640,057 B1 | 5/2017 | Ross |
| 9,707,147 B2 | 7/2017 | Levital et al. |
| D794,142 S | 8/2017 | Zhou |
| 9,717,947 B2 | 8/2017 | Lin |
| 9,737,761 B1 | 8/2017 | Govindarajan |
| 9,757,612 B2 | 9/2017 | Weber |
| 9,782,621 B2 | 10/2017 | Chiang et al. |
| 9,802,076 B2 | 10/2017 | Murray et al. |
| 9,802,081 B2 | 10/2017 | Ridgel et al. |
| 9,813,239 B2 | 11/2017 | Chee et al. |
| 9,827,445 B2 | 11/2017 | Marcos et al. |
| 9,849,337 B2 | 12/2017 | Roman et al. |
| 9,868,028 B2 | 1/2018 | Shin |
| 9,872,087 B2 | 1/2018 | DelloStritto et al. |
| 9,872,637 B2 | 1/2018 | Kording et al. |
| 9,914,053 B2 | 3/2018 | Dugan |
| 9,919,198 B2 | 3/2018 | Romeo et al. |
| 9,937,382 B2 | 4/2018 | Dugan |
| 9,939,784 B1 | 4/2018 | Berardinelli |
| 9,977,587 B2 | 5/2018 | Mountain |
| 9,993,181 B2 | 6/2018 | Ross |
| 9,997,082 B2 | 6/2018 | Kaleal |
| 10,004,946 B2 | 6/2018 | Ross |
| 10,026,052 B2 | 7/2018 | Brown et al. |
| D826,349 S | 8/2018 | Oblamski |
| 10,055,550 B2 | 8/2018 | Goetz |
| 10,058,473 B2 | 8/2018 | Oshima et al. |
| 10,074,148 B2 | 9/2018 | Cashman et al. |
| 10,089,443 B2 | 10/2018 | Miller et al. |
| 10,111,643 B2 | 10/2018 | Shulhauser et al. |
| 10,130,298 B2 | 11/2018 | Mokaya et al. |
| 10,130,311 B1 | 11/2018 | De Sapio et al. |
| 10,137,328 B2 | 11/2018 | Baudhuin |
| 10,143,395 B2 | 12/2018 | Chakravarthy et al. |
| 10,155,134 B2 | 12/2018 | Dugan |
| 10,159,872 B2 | 12/2018 | Sasaki et al. |
| 10,173,094 B2 | 1/2019 | Gomberg |
| 10,173,095 B2 | 1/2019 | Gomberg et al. |
| 10,173,096 B2 | 1/2019 | Gomberg et al. |
| 10,173,097 B2 | 1/2019 | Gomberg et al. |
| 10,198,928 B1 | 2/2019 | Ross et al. |
| 10,226,663 B2 | 3/2019 | Gomberg et al. |
| 10,231,664 B2 | 3/2019 | Ganesh |
| 10,244,990 B2 | 4/2019 | Hu et al. |
| 10,258,823 B2 | 4/2019 | Cole |
| 10,322,315 B2 | 6/2019 | Foley et al. |
| 10,325,070 B2 | 6/2019 | Beale et al. |
| 10,327,697 B1 | 6/2019 | Stein et al. |
| 10,369,021 B2 | 8/2019 | Zoss et al. |
| 10,380,866 B1 | 8/2019 | Ross et al. |
| 10,413,222 B1 | 9/2019 | Kayyali |
| 10,413,238 B1 | 9/2019 | Cooper |
| 10,424,033 B2 | 9/2019 | Romeo |
| 10,430,552 B2 | 10/2019 | Mihai |
| D866,957 S | 11/2019 | Ross et al. |
| 10,468,131 B2 | 11/2019 | Macoviak et al. |
| 10,475,323 B1 | 11/2019 | Ross |
| 10,475,537 B2 | 11/2019 | Purdie et al. |
| 10,492,977 B2 | 12/2019 | Kapure et al. |
| 10,507,358 B2 | 12/2019 | Kinnunen et al. |
| 10,542,914 B2 | 1/2020 | Forth et al. |
| 10,546,467 B1 | 1/2020 | Luciano, Jr. et al. |
| 10,569,122 B2 | 2/2020 | Johnson |
| 10,572,626 B2 | 2/2020 | Balram |
| 10,576,331 B2 | 3/2020 | Kuo |
| 10,581,896 B2 | 3/2020 | Nachenberg |
| 10,625,114 B2 | 4/2020 | Ercanbrack |
| 10,646,746 B1 | 5/2020 | Gomberg et al. |
| 10,660,534 B2 | 5/2020 | Lee et al. |
| 10,678,890 B2 | 6/2020 | Bitran et al. |
| 10,685,092 B2 | 6/2020 | Paparella et al. |
| 10,777,200 B2 | 9/2020 | Will et al. |
| D899,605 S | 10/2020 | Ross et al. |
| 10,792,495 B2 | 10/2020 | Izvorski et al. |
| 10,814,170 B2 | 10/2020 | Wang et al. |
| 10,857,426 B1 | 12/2020 | Neumann |
| 10,867,695 B2 | 12/2020 | Neagle |
| 10,874,905 B2 | 12/2020 | Belson et al. |
| D907,143 S | 1/2021 | Ach et al. |
| 10,881,911 B2 | 1/2021 | Kwon et al. |
| 10,918,332 B2 | 2/2021 | Belson et al. |
| 10,931,643 B1 | 2/2021 | Neumann |
| 10,987,176 B2 | 4/2021 | Poltaretskyi et al. |
| 10,991,463 B2 | 4/2021 | Kutzko et al. |
| 11,000,735 B2 | 5/2021 | Orady et al. |
| 11,045,709 B2 | 6/2021 | Putnam |
| 11,065,170 B2 | 7/2021 | Yang et al. |
| 11,065,527 B2 | 7/2021 | Putnam |
| 11,069,436 B2 | 7/2021 | Mason et al. |
| 11,071,597 B2 | 7/2021 | Posnack et al. |
| 11,075,000 B2 | 7/2021 | Mason et al. |
| D928,635 S | 8/2021 | Hacking et al. |
| 11,087,865 B2 | 8/2021 | Mason et al. |
| 11,094,400 B2 | 8/2021 | Riley et al. |
| 11,101,028 B2 | 8/2021 | Mason et al. |
| 11,107,591 B1 | 8/2021 | Mason |
| 11,139,060 B2 | 10/2021 | Mason et al. |
| 11,185,735 B2 | 11/2021 | Arn et al. |
| 11,185,738 B1 | 11/2021 | McKirdy et al. |
| D939,096 S | 12/2021 | Lee |
| D939,644 S | 12/2021 | Ach et al. |
| D940,797 S | 1/2022 | Ach et al. |
| D940,891 S | 1/2022 | Lee |
| 11,229,727 B2 | 1/2022 | Tatonetti |

(56) References Cited

U.S. PATENT DOCUMENTS

| | | |
|---|---|---|
| 11,265,234 B2 | 3/2022 | Guaneri et al. |
| 11,270,795 B2 | 3/2022 | Mason et al. |
| 11,272,879 B2 | 3/2022 | Wiedenhoefer et al. |
| 11,278,766 B2 | 3/2022 | Lee |
| 11,282,599 B2 | 3/2022 | Mason et al. |
| 11,282,604 B2 | 3/2022 | Mason et al. |
| 11,282,608 B2 | 3/2022 | Mason et al. |
| 11,284,797 B2 | 3/2022 | Mason et al. |
| D948,639 S | 4/2022 | Ach et al. |
| 11,295,848 B2 | 4/2022 | Mason et al. |
| 11,298,284 B2 | 4/2022 | Bayerlein |
| 11,309,085 B2 | 4/2022 | Mason et al. |
| 11,317,975 B2 | 5/2022 | Mason et al. |
| 11,325,005 B2 | 5/2022 | Mason et al. |
| 11,328,807 B2 | 5/2022 | Mason et al. |
| 11,337,648 B2 | 5/2022 | Mason |
| 11,347,829 B1* | 5/2022 | Sclar ............... G06Q 40/08 |
| 11,348,683 B2 | 5/2022 | Guaneri et al. |
| 11,376,470 B2 | 7/2022 | Weldemariam |
| 11,404,150 B2 | 8/2022 | Guaneri et al. |
| 11,410,768 B2 | 8/2022 | Mason et al. |
| 11,422,841 B2 | 8/2022 | Jeong |
| 11,437,137 B1* | 9/2022 | Harris ............... G06F 16/2237 |
| 11,495,355 B2 | 11/2022 | McNutt et al. |
| 11,508,258 B2 | 11/2022 | Nakashima et al. |
| 11,508,482 B2 | 11/2022 | Mason et al. |
| 11,515,021 B2 | 11/2022 | Mason |
| 11,515,028 B2 | 11/2022 | Mason |
| 11,524,210 B2 | 12/2022 | Kim et al. |
| 11,527,326 B2 | 12/2022 | McNair et al. |
| 11,532,402 B2 | 12/2022 | Farley et al. |
| 11,534,654 B2 | 12/2022 | Silcock et al. |
| D976,339 S | 1/2023 | Li |
| 11,541,274 B2 | 1/2023 | Hacking |
| 11,553,969 B1 | 1/2023 | Lang et al. |
| 11,621,067 B1 | 4/2023 | Nolan |
| 11,636,944 B2 | 4/2023 | Hanrahan et al. |
| 11,654,327 B2 | 5/2023 | Phillips et al. |
| 11,663,673 B2 | 5/2023 | Pyles |
| 11,701,548 B2 | 7/2023 | Posnack et al. |
| 11,957,960 B2 | 4/2024 | Bissonnette et al. |
| 12,057,210 B2 | 8/2024 | Akinola et al. |
| 12,205,704 B2 | 1/2025 | Hosoi et al. |
| 2001/0044573 A1 | 11/2001 | Manoli |
| 2002/0010596 A1 | 1/2002 | Matory |
| 2002/0072452 A1 | 6/2002 | Torkelson |
| 2002/0143279 A1 | 10/2002 | Porter et al. |
| 2002/0160883 A1 | 10/2002 | Dugan |
| 2002/0183599 A1 | 12/2002 | Castellanos |
| 2003/0013072 A1 | 1/2003 | Thomas |
| 2003/0036683 A1 | 2/2003 | Kehr et al. |
| 2003/0064860 A1 | 4/2003 | Yamashita et al. |
| 2003/0064863 A1 | 4/2003 | Chen |
| 2003/0083596 A1 | 5/2003 | Kramer et al. |
| 2003/0092536 A1 | 5/2003 | Romanelli et al. |
| 2003/0109814 A1 | 6/2003 | Rummerfield |
| 2003/0181832 A1 | 9/2003 | Carnahan et al. |
| 2004/0039260 A1* | 2/2004 | Bardy ............... A61B 5/4884 600/300 |
| 2004/0072652 A1 | 4/2004 | Alessandri et al. |
| 2004/0102931 A1 | 5/2004 | Ellis et al. |
| 2004/0106502 A1 | 6/2004 | Sher |
| 2004/0147969 A1 | 7/2004 | Mann et al. |
| 2004/0172093 A1 | 9/2004 | Rummerfield |
| 2004/0194572 A1 | 10/2004 | Kim |
| 2004/0197727 A1 | 10/2004 | Sachdeva et al. |
| 2004/0204959 A1 | 10/2004 | Moreano et al. |
| 2005/0020411 A1 | 1/2005 | Andrews |
| 2005/0043153 A1 | 2/2005 | Krietzman |
| 2005/0049122 A1 | 3/2005 | Vallone et al. |
| 2005/0085346 A1 | 4/2005 | Johnson |
| 2005/0085353 A1 | 4/2005 | Johnson |
| 2005/0115561 A1 | 6/2005 | Stahmann |
| 2005/0143641 A1 | 6/2005 | Tashiro |
| 2005/0274220 A1 | 12/2005 | Reboullet |
| 2006/0003871 A1 | 1/2006 | Houghton |
| 2006/0009332 A1* | 1/2006 | Jones ............... A63B 24/0062 482/54 |
| 2006/0046905 A1 | 3/2006 | Doody, Jr. et al. |
| 2006/0058648 A1 | 3/2006 | Meier |
| 2006/0064136 A1 | 3/2006 | Wang |
| 2006/0064329 A1 | 3/2006 | Abolfathi et al. |
| 2006/0129432 A1* | 6/2006 | Choi ............... A61B 5/0002 600/300 |
| 2006/0199700 A1 | 9/2006 | LaStayo et al. |
| 2006/0247095 A1 | 11/2006 | Rummerfield |
| 2007/0016444 A1* | 1/2007 | Holkkola ............... G16H 40/40 482/8 |
| 2007/0042868 A1 | 2/2007 | Fisher et al. |
| 2007/0050187 A1* | 3/2007 | Cox ............... G06Q 10/10 704/9 |
| 2007/0118389 A1 | 5/2007 | Shipon |
| 2007/0137307 A1 | 6/2007 | Gruben et al. |
| 2007/0173392 A1 | 7/2007 | Stanford |
| 2007/0184414 A1 | 8/2007 | Perez |
| 2007/0194939 A1 | 8/2007 | Alvarez et al. |
| 2007/0219059 A1 | 9/2007 | Schwartz |
| 2007/0271065 A1 | 11/2007 | Gupta et al. |
| 2007/0282228 A1* | 12/2007 | Einav ............... A63B 21/00181 600/300 |
| 2007/0287597 A1 | 12/2007 | Cameron |
| 2008/0021834 A1 | 1/2008 | Holla et al. |
| 2008/0077619 A1 | 3/2008 | Gilley et al. |
| 2008/0082356 A1 | 4/2008 | Friedlander et al. |
| 2008/0096726 A1 | 4/2008 | Riley et al. |
| 2008/0153592 A1 | 6/2008 | James-Herbert |
| 2008/0161166 A1 | 7/2008 | Lo |
| 2008/0161733 A1 | 7/2008 | Einav et al. |
| 2008/0183500 A1 | 7/2008 | Banigan |
| 2008/0281633 A1 | 11/2008 | Burdea et al. |
| 2008/0300914 A1 | 12/2008 | Karkanias et al. |
| 2009/0011907 A1 | 1/2009 | Radow et al. |
| 2009/0058635 A1 | 3/2009 | LaLonde et al. |
| 2009/0069643 A1* | 3/2009 | Quy ............... A61B 5/0022 600/300 |
| 2009/0070138 A1 | 3/2009 | Langheier et al. |
| 2009/0211395 A1 | 8/2009 | Mul'e |
| 2009/0270227 A1 | 10/2009 | Ashby et al. |
| 2009/0287503 A1 | 11/2009 | Angell et al. |
| 2009/0299766 A1 | 12/2009 | Friedlander et al. |
| 2010/0048358 A1 | 2/2010 | Tchao et al. |
| 2010/0076786 A1 | 3/2010 | Dalton et al. |
| 2010/0121160 A1 | 5/2010 | Stark et al. |
| 2010/0173747 A1 | 7/2010 | Chen et al. |
| 2010/0216168 A1 | 8/2010 | Heinzman et al. |
| 2010/0234184 A1 | 9/2010 | Le Page et al. |
| 2010/0248899 A1 | 9/2010 | Bedell et al. |
| 2010/0248905 A1 | 9/2010 | Lu |
| 2010/0262052 A1 | 10/2010 | Lunau et al. |
| 2010/0268304 A1 | 10/2010 | Matos |
| 2010/0298102 A1 | 11/2010 | Bosecker et al. |
| 2010/0326207 A1 | 12/2010 | Topel |
| 2011/0010188 A1 | 1/2011 | Yoshikawa et al. |
| 2011/0015042 A1* | 1/2011 | Jaquish ............... A63B 24/00 482/9 |
| 2011/0047108 A1 | 2/2011 | Chakrabarty et al. |
| 2011/0119212 A1 | 5/2011 | De Bruin et al. |
| 2011/0172059 A1 | 7/2011 | Watterson et al. |
| 2011/0195819 A1 | 8/2011 | Shaw et al. |
| 2011/0218814 A1 | 9/2011 | Coats |
| 2011/0275483 A1 | 11/2011 | Dugan |
| 2011/0281249 A1 | 11/2011 | Gammell et al. |
| 2011/0306846 A1 | 12/2011 | Osorio |
| 2012/0041771 A1 | 2/2012 | Cosentino et al. |
| 2012/0065987 A1 | 3/2012 | Farooq et al. |
| 2012/0116258 A1 | 5/2012 | Lee |
| 2012/0130196 A1 | 5/2012 | Jain et al. |
| 2012/0130197 A1 | 5/2012 | Kugler et al. |
| 2012/0166212 A1* | 6/2012 | Campbell ............... G16H 50/20 705/2 |
| 2012/0167709 A1 | 7/2012 | Chen et al. |
| 2012/0183939 A1 | 7/2012 | Aragones et al. |
| 2012/0190502 A1 | 7/2012 | Paulus et al. |

(56) References Cited

U.S. PATENT DOCUMENTS

| | | |
|---|---|---|
| 2012/0232438 A1 | 9/2012 | Cataldi et al. |
| 2012/0259648 A1 | 10/2012 | Mallon et al. |
| 2012/0259649 A1* | 10/2012 | Mallon ............... G16H 40/63 705/2 |
| 2012/0278759 A1 | 11/2012 | Curl et al. |
| 2012/0295240 A1 | 11/2012 | Walker et al. |
| 2012/0296455 A1 | 11/2012 | Ohnemus et al. |
| 2012/0310667 A1 | 12/2012 | Altman et al. |
| 2013/0108594 A1 | 5/2013 | Martin-Rendon et al. |
| 2013/0110545 A1 | 5/2013 | Smallwood |
| 2013/0123667 A1 | 5/2013 | Komatireddy et al. |
| 2013/0137550 A1 | 5/2013 | Skinner et al. |
| 2013/0137552 A1 | 5/2013 | Kemp et al. |
| 2013/0178334 A1 | 7/2013 | Brammer |
| 2013/0211281 A1 | 8/2013 | Ross et al. |
| 2013/0241696 A1* | 9/2013 | Fabrizio ............... G16H 20/30 340/5.81 |
| 2013/0253943 A1 | 9/2013 | Lee et al. |
| 2013/0274069 A1 | 10/2013 | Watterson et al. |
| 2013/0296987 A1 | 11/2013 | Rogers et al. |
| 2013/0318027 A1 | 11/2013 | Almogy et al. |
| 2013/0332616 A1 | 12/2013 | Landwehr |
| 2013/0345025 A1 | 12/2013 | van der Merwe |
| 2014/0006042 A1 | 1/2014 | Keefe et al. |
| 2014/0011640 A1 | 1/2014 | Dugan |
| 2014/0031174 A1 | 1/2014 | Huang |
| 2014/0062900 A1 | 3/2014 | Kaula et al. |
| 2014/0074179 A1 | 3/2014 | Heldman et al. |
| 2014/0089836 A1 | 3/2014 | Damani et al. |
| 2014/0113261 A1 | 4/2014 | Akiba |
| 2014/0113768 A1 | 4/2014 | Lin et al. |
| 2014/0155129 A1 | 6/2014 | Dugan |
| 2014/0163439 A1 | 6/2014 | Uryash et al. |
| 2014/0172442 A1 | 6/2014 | Broderick |
| 2014/0172460 A1 | 6/2014 | Kohli |
| 2014/0172514 A1 | 6/2014 | Schumann et al. |
| 2014/0188009 A1 | 7/2014 | Lange et al. |
| 2014/0194250 A1 | 7/2014 | Reich et al. |
| 2014/0194251 A1 | 7/2014 | Reich et al. |
| 2014/0207264 A1 | 7/2014 | Quy |
| 2014/0207486 A1 | 7/2014 | Carty et al. |
| 2014/0228649 A1 | 8/2014 | Rayner et al. |
| 2014/0246499 A1 | 9/2014 | Proud et al. |
| 2014/0256511 A1 | 9/2014 | Smith |
| 2014/0257837 A1 | 9/2014 | Walker et al. |
| 2014/0274565 A1 | 9/2014 | Boyette et al. |
| 2014/0274622 A1 | 9/2014 | Leonhard |
| 2014/0303540 A1 | 10/2014 | Baym |
| 2014/0309083 A1 | 10/2014 | Dugan |
| 2014/0315689 A1 | 10/2014 | Vauquelin et al. |
| 2014/0322686 A1 | 10/2014 | Kang |
| 2014/0347265 A1 | 11/2014 | Aimone et al. |
| 2014/0371816 A1 | 12/2014 | Matos |
| 2014/0372133 A1 | 12/2014 | Austrum et al. |
| 2015/0025816 A1 | 1/2015 | Ross |
| 2015/0045700 A1 | 2/2015 | Cavanagh et al. |
| 2015/0051721 A1 | 2/2015 | Cheng |
| 2015/0065213 A1 | 3/2015 | Dugan |
| 2015/0073814 A1 | 3/2015 | Linebaugh |
| 2015/0088544 A1 | 3/2015 | Goldberg |
| 2015/0094192 A1 | 4/2015 | Skwortsow et al. |
| 2015/0099458 A1 | 4/2015 | Weisner et al. |
| 2015/0099952 A1 | 4/2015 | Lain et al. |
| 2015/0111644 A1 | 4/2015 | Larson |
| 2015/0112230 A1 | 4/2015 | Iglesias |
| 2015/0112702 A1 | 4/2015 | Joao et al. |
| 2015/0130830 A1 | 5/2015 | Nagasaki |
| 2015/0141200 A1 | 5/2015 | Murray et al. |
| 2015/0142142 A1 | 5/2015 | Campana Aguilera et al. |
| 2015/0149217 A1 | 5/2015 | Kaburagi |
| 2015/0151162 A1 | 6/2015 | Dugan |
| 2015/0157938 A1 | 6/2015 | Domansky et al. |
| 2015/0158549 A1 | 6/2015 | Gros et al. |
| 2015/0161331 A1 | 6/2015 | Oleynik |
| 2015/0161876 A1 | 6/2015 | Castillo |
| 2015/0174446 A1 | 6/2015 | Chiang |
| 2015/0196805 A1 | 7/2015 | Koduri |
| 2015/0217056 A1 | 8/2015 | Kadavy et al. |
| 2015/0251074 A1 | 9/2015 | Ahmed et al. |
| 2015/0257679 A1 | 9/2015 | Ross |
| 2015/0265209 A1 | 9/2015 | Zhang |
| 2015/0290061 A1 | 10/2015 | Stafford et al. |
| 2015/0302766 A1* | 10/2015 | Oberlander ............ G06Q 10/10 434/247 |
| 2015/0339442 A1 | 11/2015 | Oleynik |
| 2015/0341812 A1 | 11/2015 | Dion et al. |
| 2015/0351664 A1 | 12/2015 | Ross |
| 2015/0351665 A1 | 12/2015 | Ross |
| 2015/0356647 A1* | 12/2015 | Reiser ................... G06Q 30/04 705/3 |
| 2015/0360069 A1 | 12/2015 | Marti et al. |
| 2015/0379232 A1 | 12/2015 | Mainwaring et al. |
| 2015/0379430 A1 | 12/2015 | Dirac et al. |
| 2016/0004820 A1 | 1/2016 | Moore |
| 2016/0007885 A1 | 1/2016 | Basta |
| 2016/0015995 A1 | 1/2016 | Leung et al. |
| 2016/0023081 A1 | 1/2016 | Popa-Simil |
| 2016/0045170 A1 | 2/2016 | Migita |
| 2016/0096073 A1 | 4/2016 | Rahman et al. |
| 2016/0117471 A1 | 4/2016 | Belt et al. |
| 2016/0132643 A1 | 5/2016 | Radhakrishna et al. |
| 2016/0140319 A1 | 5/2016 | Stark et al. |
| 2016/0143593 A1 | 5/2016 | Fu et al. |
| 2016/0151670 A1 | 6/2016 | Dugan |
| 2016/0158534 A1 | 6/2016 | Guarraia et al. |
| 2016/0166833 A1 | 6/2016 | Bum |
| 2016/0166881 A1 | 6/2016 | Ridgel et al. |
| 2016/0193306 A1 | 7/2016 | Rabovsky et al. |
| 2016/0197918 A1 | 7/2016 | Turgeman et al. |
| 2016/0213924 A1 | 7/2016 | Coleman |
| 2016/0275259 A1 | 9/2016 | Nolan et al. |
| 2016/0287166 A1 | 10/2016 | Tran |
| 2016/0292370 A1* | 10/2016 | Saric .................... G16H 40/67 |
| 2016/0302666 A1 | 10/2016 | Shaya |
| 2016/0302721 A1 | 10/2016 | Wiedenhoefer et al. |
| 2016/0317869 A1 | 11/2016 | Dugan |
| 2016/0322078 A1 | 11/2016 | Bose et al. |
| 2016/0325140 A1 | 11/2016 | Wu |
| 2016/0332028 A1 | 11/2016 | Melnik |
| 2016/0345841 A1 | 12/2016 | Jang et al. |
| 2016/0354636 A1 | 12/2016 | Jang |
| 2016/0361025 A1 | 12/2016 | Reicher et al. |
| 2016/0361597 A1 | 12/2016 | Cole et al. |
| 2016/0373477 A1 | 12/2016 | Moyle |
| 2017/0004260 A1 | 1/2017 | Moturu et al. |
| 2017/0011179 A1 | 1/2017 | Arshad et al. |
| 2017/0032092 A1* | 2/2017 | Mink .................. G06Q 10/1095 |
| 2017/0033375 A1 | 2/2017 | Ohmori et al. |
| 2017/0042467 A1 | 2/2017 | Herr et al. |
| 2017/0046488 A1 | 2/2017 | Pereira |
| 2017/0065851 A1 | 3/2017 | Deluca et al. |
| 2017/0080320 A1 | 3/2017 | Smith |
| 2017/0091422 A1 | 3/2017 | Kumar et al. |
| 2017/0095670 A1 | 4/2017 | Ghaffari et al. |
| 2017/0095692 A1 | 4/2017 | Chang et al. |
| 2017/0095693 A1 | 4/2017 | Chang et al. |
| 2017/0100637 A1 | 4/2017 | Princen et al. |
| 2017/0106242 A1 | 4/2017 | Dugan |
| 2017/0109500 A1* | 4/2017 | Raynor ............... G06Q 10/1097 |
| 2017/0113092 A1 | 4/2017 | Johnson |
| 2017/0128769 A1 | 5/2017 | Long et al. |
| 2017/0132947 A1 | 5/2017 | Maeda et al. |
| 2017/0136296 A1 | 5/2017 | Barrera et al. |
| 2017/0143261 A1 | 5/2017 | Wiedenhoefer et al. |
| 2017/0147752 A1 | 5/2017 | Toru |
| 2017/0147789 A1 | 5/2017 | Wiedenhoefer et al. |
| 2017/0148297 A1 | 5/2017 | Ross |
| 2017/0168555 A1 | 6/2017 | Munoz et al. |
| 2017/0181698 A1 | 6/2017 | Wiedenhoefer et al. |
| 2017/0185893 A1* | 6/2017 | Wetta ................... G16H 40/20 |
| 2017/0190052 A1 | 7/2017 | Jaekel et al. |
| 2017/0202724 A1 | 7/2017 | De Rossi |
| 2017/0209766 A1 | 7/2017 | Riley et al. |
| 2017/0220751 A1 | 8/2017 | Davis |

(56) References Cited

U.S. PATENT DOCUMENTS

| | | |
|---|---|---|
| 2017/0228517 A1* | 8/2017 | Saliman ................ G16H 10/20 |
| 2017/0235882 A1 | 8/2017 | Orlov et al. |
| 2017/0235884 A1* | 8/2017 | Harmon ................ G16H 40/20 705/2 |
| 2017/0235906 A1 | 8/2017 | Dorris et al. |
| 2017/0243028 A1 | 8/2017 | LaFever et al. |
| 2017/0258370 A1 | 9/2017 | Plotnik-Peleg et al. |
| 2017/0262604 A1 | 9/2017 | Francois |
| 2017/0266501 A1 | 9/2017 | Sanders et al. |
| 2017/0270260 A1 | 9/2017 | Shetty |
| 2017/0278209 A1 | 9/2017 | Olsen et al. |
| 2017/0282015 A1 | 10/2017 | Wicks et al. |
| 2017/0283508 A1 | 10/2017 | Demopulos et al. |
| 2017/0286621 A1 | 10/2017 | Cox |
| 2017/0296861 A1 | 10/2017 | Burkinshaw |
| 2017/0300654 A1 | 10/2017 | Stein et al. |
| 2017/0304024 A1 | 10/2017 | Nobrega |
| 2017/0312614 A1 | 11/2017 | Tran et al. |
| 2017/0323481 A1 | 11/2017 | Tran et al. |
| 2017/0329917 A1 | 11/2017 | McRaith et al. |
| 2017/0329933 A1 | 11/2017 | Brust |
| 2017/0333755 A1 | 11/2017 | Rider |
| 2017/0337033 A1 | 11/2017 | Duyan et al. |
| 2017/0337334 A1 | 11/2017 | Stanczak |
| 2017/0344726 A1 | 11/2017 | Duffy et al. |
| 2017/0347923 A1 | 12/2017 | Roh |
| 2017/0360586 A1 | 12/2017 | Dempers et al. |
| 2017/0368413 A1 | 12/2017 | Shavit |
| 2017/0372029 A1* | 12/2017 | Saliman ................ G16H 10/60 |
| 2018/0017806 A1 | 1/2018 | Wang et al. |
| 2018/0036591 A1 | 2/2018 | King et al. |
| 2018/0036593 A1 | 2/2018 | Ridgel et al. |
| 2018/0052962 A1 | 2/2018 | Van Der Koijk et al. |
| 2018/0056104 A1 | 3/2018 | Cromie et al. |
| 2018/0056130 A1 | 3/2018 | Bitran et al. |
| 2018/0060494 A1 | 3/2018 | Dias et al. |
| 2018/0071565 A1 | 3/2018 | Gomberg et al. |
| 2018/0071566 A1 | 3/2018 | Gomberg et al. |
| 2018/0071569 A1 | 3/2018 | Gomberg et al. |
| 2018/0071570 A1 | 3/2018 | Gomberg et al. |
| 2018/0071571 A1 | 3/2018 | Gomberg et al. |
| 2018/0071572 A1 | 3/2018 | Gomberg et al. |
| 2018/0075192 A1* | 3/2018 | Sethumadhavan .... G06Q 40/08 |
| 2018/0075205 A1 | 3/2018 | Moturu et al. |
| 2018/0078843 A1 | 3/2018 | Tran et al. |
| 2018/0081859 A1* | 3/2018 | Snider .................... G06F 40/44 |
| 2018/0085615 A1 | 3/2018 | Astolfi et al. |
| 2018/0096111 A1 | 4/2018 | Wells et al. |
| 2018/0099178 A1 | 4/2018 | Schaefer et al. |
| 2018/0102190 A1 | 4/2018 | Hogue et al. |
| 2018/0113985 A1 | 4/2018 | Gandy et al. |
| 2018/0116741 A1 | 5/2018 | Garcia Kilroy et al. |
| 2018/0117417 A1 | 5/2018 | Davis |
| 2018/0130555 A1 | 5/2018 | Chronis et al. |
| 2018/0140927 A1 | 5/2018 | Kito |
| 2018/0146870 A1 | 5/2018 | Shemesh |
| 2018/0177612 A1 | 6/2018 | Trabish et al. |
| 2018/0178061 A1 | 6/2018 | O'larte et al. |
| 2018/0199855 A1 | 7/2018 | Odame et al. |
| 2018/0200577 A1 | 7/2018 | Dugan |
| 2018/0220935 A1 | 8/2018 | Tadano et al. |
| 2018/0228682 A1 | 8/2018 | Bayerlein et al. |
| 2018/0232492 A1 | 8/2018 | Al-Alul et al. |
| 2018/0236307 A1 | 8/2018 | Hyde et al. |
| 2018/0240552 A1 | 8/2018 | Tuyl et al. |
| 2018/0253991 A1 | 9/2018 | Tang et al. |
| 2018/0255110 A1 | 9/2018 | Dowlatkhah et al. |
| 2018/0256079 A1 | 9/2018 | Yang et al. |
| 2018/0263530 A1 | 9/2018 | Jung |
| 2018/0263535 A1 | 9/2018 | Cramer |
| 2018/0263552 A1 | 9/2018 | Graman et al. |
| 2018/0264312 A1 | 9/2018 | Pompile et al. |
| 2018/0271432 A1 | 9/2018 | Auchinleck et al. |
| 2018/0272184 A1 | 9/2018 | Vassilaros et al. |
| 2018/0280784 A1 | 10/2018 | Romeo et al. |
| 2018/0296143 A1 | 10/2018 | Anderson et al. |
| 2018/0296157 A1 | 10/2018 | Bleich et al. |
| 2018/0318122 A1 | 11/2018 | LeCursi et al. |
| 2018/0326243 A1 | 11/2018 | Badi et al. |
| 2018/0330058 A1 | 11/2018 | Bates |
| 2018/0330810 A1 | 11/2018 | Gamarnik |
| 2018/0330824 A1 | 11/2018 | Athey et al. |
| 2018/0290017 A1 | 12/2018 | Fung |
| 2018/0353812 A1 | 12/2018 | Lannon et al. |
| 2018/0360340 A1 | 12/2018 | Rehse et al. |
| 2018/0366225 A1 | 12/2018 | Mansi et al. |
| 2018/0373844 A1 | 12/2018 | Ferrandez-Escamez et al. |
| 2019/0009135 A1 | 1/2019 | Wu |
| 2019/0019163 A1 | 1/2019 | Batey et al. |
| 2019/0019573 A1 | 1/2019 | Lake et al. |
| 2019/0019578 A1 | 1/2019 | Vaccaro |
| 2019/0030415 A1 | 1/2019 | Volpe, Jr. |
| 2019/0031284 A1 | 1/2019 | Fuchs |
| 2019/0038187 A1* | 2/2019 | Latella, Jr. ............ G06F 3/0346 |
| 2019/0046794 A1 | 2/2019 | Goodall et al. |
| 2019/0060708 A1 | 2/2019 | Fung |
| 2019/0065970 A1 | 2/2019 | Bonutti et al. |
| 2019/0066832 A1 | 2/2019 | Kang et al. |
| 2019/0076701 A1 | 3/2019 | Dugan |
| 2019/0080802 A1 | 3/2019 | Ziobro et al. |
| 2019/0083846 A1 | 3/2019 | Eder |
| 2019/0088356 A1 | 3/2019 | Oliver et al. |
| 2019/0090744 A1 | 3/2019 | Mahfouz |
| 2019/0096534 A1 | 3/2019 | Joao |
| 2019/0105551 A1 | 4/2019 | Ray |
| 2019/0111299 A1 | 4/2019 | Radcliffe et al. |
| 2019/0115097 A1 | 4/2019 | Macoviak et al. |
| 2019/0117156 A1 | 4/2019 | Howard et al. |
| 2019/0118038 A1 | 4/2019 | Tana et al. |
| 2019/0126099 A1 | 5/2019 | Hoang |
| 2019/0132948 A1 | 5/2019 | Longinotti-Buitoni et al. |
| 2019/0134454 A1 | 5/2019 | Mahoney et al. |
| 2019/0137988 A1 | 5/2019 | Cella et al. |
| 2019/0143191 A1 | 5/2019 | Ran et al. |
| 2019/0145774 A1 | 5/2019 | Ellis |
| 2019/0163876 A1 | 5/2019 | Remme et al. |
| 2019/0167988 A1 | 6/2019 | Shahriari et al. |
| 2019/0172587 A1 | 6/2019 | Park et al. |
| 2019/0175988 A1 | 6/2019 | Volterrani et al. |
| 2019/0183715 A1 | 6/2019 | Kapure et al. |
| 2019/0200920 A1 | 7/2019 | Tien et al. |
| 2019/0209891 A1 | 7/2019 | Fung |
| 2019/0214119 A1 | 7/2019 | Wachira et al. |
| 2019/0223797 A1 | 7/2019 | Tran |
| 2019/0224528 A1 | 7/2019 | Omid-Zohoor et al. |
| 2019/0228856 A1 | 7/2019 | Leifer |
| 2019/0232108 A1 | 8/2019 | Kovach et al. |
| 2019/0240103 A1 | 8/2019 | Hepler et al. |
| 2019/0240541 A1 | 8/2019 | Denton et al. |
| 2019/0244540 A1 | 8/2019 | Errante et al. |
| 2019/0251456 A1 | 8/2019 | Constantin |
| 2019/0261959 A1 | 8/2019 | Frankel |
| 2019/0262084 A1 | 8/2019 | Roh |
| 2019/0269343 A1 | 9/2019 | Ramos Murguialday et al. |
| 2019/0274523 A1 | 9/2019 | Bates et al. |
| 2019/0275368 A1 | 9/2019 | Maroldi |
| 2019/0290964 A1 | 9/2019 | Oren |
| 2019/0304584 A1 | 10/2019 | Savolainen |
| 2019/0307983 A1 | 10/2019 | Goldman |
| 2019/0314681 A1 | 10/2019 | Yang |
| 2019/0344123 A1 | 11/2019 | Rubin et al. |
| 2019/0354632 A1 | 11/2019 | Mital et al. |
| 2019/0362242 A1 | 11/2019 | Pillai et al. |
| 2019/0366146 A1 | 12/2019 | Tong et al. |
| 2019/0385199 A1 | 12/2019 | Bender et al. |
| 2019/0388728 A1 | 12/2019 | Wang et al. |
| 2019/0392936 A1 | 12/2019 | Arric et al. |
| 2019/0392939 A1 | 12/2019 | Basta et al. |
| 2020/0005928 A1 | 1/2020 | Daniel |
| 2020/0034707 A1 | 1/2020 | Kivatinos et al. |
| 2020/0038703 A1 | 2/2020 | Cleary et al. |
| 2020/0051446 A1 | 2/2020 | Rubinstein et al. |
| 2020/0066390 A1 | 2/2020 | Svendrys et al. |
| 2020/0085300 A1 | 3/2020 | Kwatra et al. |

(56) References Cited

U.S. PATENT DOCUMENTS

| | | |
|---|---|---|
| 2020/0090802 A1 | 3/2020 | Maron |
| 2020/0093418 A1 | 3/2020 | Kluger et al. |
| 2020/0118682 A1* | 4/2020 | Villazón-Terrazas ........................ G06N 20/00 |
| 2020/0143922 A1 | 5/2020 | Chekroud et al. |
| 2020/0151595 A1 | 5/2020 | Jayalath et al. |
| 2020/0151646 A1 | 5/2020 | De La Fuente Sanchez |
| 2020/0152339 A1 | 5/2020 | Pulitzer et al. |
| 2020/0160198 A1 | 5/2020 | Reeves et al. |
| 2020/0170876 A1 | 6/2020 | Kapure et al. |
| 2020/0176098 A1 | 6/2020 | Lucas et al. |
| 2020/0197744 A1 | 6/2020 | Schweighofer |
| 2020/0221975 A1 | 7/2020 | Basta et al. |
| 2020/0237291 A1 | 7/2020 | Raja |
| 2020/0237452 A1* | 7/2020 | Wolf ........................ G06F 3/048 |
| 2020/0265746 A1* | 8/2020 | Derwinger ............... G09B 5/02 |
| 2020/0267487 A1 | 8/2020 | Siva |
| 2020/0275886 A1 | 9/2020 | Mason |
| 2020/0289045 A1 | 9/2020 | Hacking et al. |
| 2020/0289046 A1 | 9/2020 | Hacking et al. |
| 2020/0289879 A1 | 9/2020 | Hacking et al. |
| 2020/0289880 A1 | 9/2020 | Hacking et al. |
| 2020/0289881 A1 | 9/2020 | Hacking et al. |
| 2020/0289889 A1 | 9/2020 | Hacking et al. |
| 2020/0293712 A1 | 9/2020 | Potts et al. |
| 2020/0303063 A1 | 9/2020 | Sharma et al. |
| 2020/0312447 A1* | 10/2020 | Bohn ............. G06Q 10/063112 |
| 2020/0334972 A1 | 10/2020 | Gopalakrishnan |
| 2020/0353314 A1 | 11/2020 | Messinger |
| 2020/0357299 A1 | 11/2020 | Patel et al. |
| 2020/0365256 A1 | 11/2020 | Hayashitani et al. |
| 2020/0395112 A1 | 12/2020 | Ronner |
| 2020/0398083 A1 | 12/2020 | Adelsheim |
| 2020/0401224 A1 | 12/2020 | Cotton |
| 2020/0402662 A1 | 12/2020 | Esmailian et al. |
| 2020/0410374 A1* | 12/2020 | White .................... G16H 40/67 |
| 2020/0410385 A1 | 12/2020 | Otsuki |
| 2020/0411162 A1 | 12/2020 | Lien et al. |
| 2021/0005224 A1 | 1/2021 | Rothschild et al. |
| 2021/0005319 A1 | 1/2021 | Otsuki et al. |
| 2021/0008413 A1* | 1/2021 | Asikainen ............. G06F 3/0304 |
| 2021/0015560 A1 | 1/2021 | Boddington et al. |
| 2021/0027889 A1* | 1/2021 | Neil ........................ G16H 10/60 |
| 2021/0035674 A1 | 2/2021 | Volosin et al. |
| 2021/0050086 A1 | 2/2021 | Rose et al. |
| 2021/0065855 A1 | 3/2021 | Pepin et al. |
| 2021/0074178 A1 | 3/2021 | Ilan et al. |
| 2021/0076981 A1 | 3/2021 | Hacking et al. |
| 2021/0077860 A1 | 3/2021 | Posnack et al. |
| 2021/0077884 A1 | 3/2021 | De Las Casas Zolezzi et al. |
| 2021/0082554 A1 | 3/2021 | Kalia et al. |
| 2021/0093891 A1 | 4/2021 | Sheng |
| 2021/0098129 A1 | 4/2021 | Neumann |
| 2021/0101051 A1 | 4/2021 | Posnack et al. |
| 2021/0113890 A1 | 4/2021 | Posnack et al. |
| 2021/0125696 A1 | 4/2021 | Liu et al. |
| 2021/0127974 A1 | 5/2021 | Mason et al. |
| 2021/0128080 A1 | 5/2021 | Mason et al. |
| 2021/0128255 A1 | 5/2021 | Mason et al. |
| 2021/0128978 A1 | 5/2021 | Gilstrom et al. |
| 2021/0134412 A1 | 5/2021 | Guaneri et al. |
| 2021/0134425 A1 | 5/2021 | Mason et al. |
| 2021/0134428 A1 | 5/2021 | Mason et al. |
| 2021/0134430 A1 | 5/2021 | Mason et al. |
| 2021/0134432 A1 | 5/2021 | Mason et al. |
| 2021/0134456 A1 | 5/2021 | Posnack et al. |
| 2021/0134457 A1 | 5/2021 | Mason et al. |
| 2021/0134458 A1 | 5/2021 | Mason et al. |
| 2021/0134463 A1 | 5/2021 | Mason et al. |
| 2021/0138304 A1 | 5/2021 | Mason et al. |
| 2021/0142875 A1 | 5/2021 | Mason et al. |
| 2021/0142898 A1 | 5/2021 | Mason et al. |
| 2021/0142903 A1 | 5/2021 | Mason et al. |
| 2021/0144074 A1 | 5/2021 | Guaneri et al. |
| 2021/0186419 A1 | 6/2021 | Van Ee et al. |
| 2021/0187348 A1 | 6/2021 | Phillips et al. |
| 2021/0187353 A1* | 6/2021 | Eder ...................... G16H 20/30 |
| 2021/0202090 A1 | 7/2021 | ODonovan et al. |
| 2021/0202103 A1 | 7/2021 | Bostic et al. |
| 2021/0236020 A1 | 8/2021 | Matijevich et al. |
| 2021/0244998 A1 | 8/2021 | Hacking et al. |
| 2021/0245003 A1 | 8/2021 | Turner |
| 2021/0251562 A1 | 8/2021 | Jain |
| 2021/0272677 A1 | 9/2021 | Barbee |
| 2021/0338469 A1 | 11/2021 | Dempers |
| 2021/0343384 A1 | 11/2021 | Purushothaman et al. |
| 2021/0345879 A1 | 11/2021 | Mason et al. |
| 2021/0345975 A1 | 11/2021 | Mason et al. |
| 2021/0350888 A1 | 11/2021 | Guaneri et al. |
| 2021/0350898 A1 | 11/2021 | Mason et al. |
| 2021/0350899 A1 | 11/2021 | Mason et al. |
| 2021/0350901 A1 | 11/2021 | Mason et al. |
| 2021/0350902 A1 | 11/2021 | Mason et al. |
| 2021/0350914 A1 | 11/2021 | Guaneri et al. |
| 2021/0350926 A1 | 11/2021 | Mason et al. |
| 2021/0361514 A1 | 11/2021 | Choi et al. |
| 2021/0366587 A1 | 11/2021 | Mason et al. |
| 2021/0377346 A1* | 12/2021 | Zhou ...................... H04W 4/80 |
| 2021/0383909 A1 | 12/2021 | Mason et al. |
| 2021/0391091 A1 | 12/2021 | Mason |
| 2021/0398668 A1 | 12/2021 | Chock et al. |
| 2021/0407670 A1 | 12/2021 | Mason et al. |
| 2021/0407681 A1 | 12/2021 | Mason et al. |
| 2022/0000556 A1 | 1/2022 | Casey et al. |
| 2022/0015838 A1 | 1/2022 | Posnack et al. |
| 2022/0016480 A1 | 1/2022 | Bissonnette et al. |
| 2022/0016482 A1 | 1/2022 | Bissonnette |
| 2022/0016485 A1 | 1/2022 | Bissonnette et al. |
| 2022/0016486 A1 | 1/2022 | Bissonnette |
| 2022/0020469 A1 | 1/2022 | Tanner |
| 2022/0044806 A1 | 2/2022 | Sanders et al. |
| 2022/0047921 A1 | 2/2022 | Bissonnette et al. |
| 2022/0079690 A1 | 3/2022 | Mason et al. |
| 2022/0080256 A1 | 3/2022 | Arn et al. |
| 2022/0080265 A1 | 3/2022 | Watterson |
| 2022/0105384 A1 | 4/2022 | Hacking et al. |
| 2022/0105385 A1 | 4/2022 | Hacking et al. |
| 2022/0105390 A1 | 4/2022 | Yuasa |
| 2022/0115133 A1 | 4/2022 | Mason et al. |
| 2022/0118218 A1 | 4/2022 | Bense et al. |
| 2022/0122724 A1 | 4/2022 | Durlach et al. |
| 2022/0126169 A1 | 4/2022 | Mason |
| 2022/0133576 A1 | 5/2022 | Choi et al. |
| 2022/0148725 A1 | 5/2022 | Mason et al. |
| 2022/0158916 A1 | 5/2022 | Mason et al. |
| 2022/0176039 A1 | 6/2022 | Lintereur et al. |
| 2022/0181004 A1 | 6/2022 | Zilca et al. |
| 2022/0193491 A1 | 6/2022 | Mason et al. |
| 2022/0230729 A1 | 7/2022 | Mason |
| 2022/0238222 A1 | 7/2022 | Neuberg |
| 2022/0238223 A1 | 7/2022 | Mason et al. |
| 2022/0258935 A1 | 8/2022 | Kraft |
| 2022/0262483 A1 | 8/2022 | Rosenberg et al. |
| 2022/0262504 A1 | 8/2022 | Bratty et al. |
| 2022/0266094 A1 | 8/2022 | Mason et al. |
| 2022/0270738 A1 | 8/2022 | Mason et al. |
| 2022/0273985 A1 | 9/2022 | Jeong et al. |
| 2022/0273986 A1 | 9/2022 | Mason |
| 2022/0288460 A1 | 9/2022 | Mason |
| 2022/0288461 A1 | 9/2022 | Ashley et al. |
| 2022/0288462 A1 | 9/2022 | Ashley et al. |
| 2022/0293257 A1 | 9/2022 | Guaneri et al. |
| 2022/0300787 A1 | 9/2022 | Wall et al. |
| 2022/0304881 A1 | 9/2022 | Choi et al. |
| 2022/0304882 A1 | 9/2022 | Choi |
| 2022/0305328 A1 | 9/2022 | Choi et al. |
| 2022/0314072 A1 | 10/2022 | Bissonnette et al. |
| 2022/0314075 A1 | 10/2022 | Mason et al. |
| 2022/0323826 A1 | 10/2022 | Khurana |
| 2022/0327714 A1 | 10/2022 | Cook et al. |
| 2022/0327807 A1 | 10/2022 | Cook et al. |
| 2022/0328181 A1 | 10/2022 | Mason et al. |
| 2022/0330823 A1 | 10/2022 | Janssen |
| 2022/0331663 A1 | 10/2022 | Mason |

(56) References Cited

U.S. PATENT DOCUMENTS

| | | | |
|---|---|---|---|
| 2022/0338761 A1 | 10/2022 | Maddahi et al. |
| 2022/0339052 A1 | 10/2022 | Kim |
| 2022/0339501 A1 | 10/2022 | Mason et al. |
| 2022/0370851 A1 | 11/2022 | Guidarelli et al. |
| 2022/0384012 A1 | 12/2022 | Mason |
| 2022/0392591 A1 | 12/2022 | Guaneri et al. |
| 2022/0395232 A1 | 12/2022 | Locke |
| 2022/0401783 A1 | 12/2022 | Choi |
| 2022/0415469 A1 | 12/2022 | Mason |
| 2022/0415471 A1 | 12/2022 | Mason |
| 2023/0001268 A1 | 1/2023 | Bissonnette et al. |
| 2023/0013530 A1 | 1/2023 | Mason |
| 2023/0014598 A1 | 1/2023 | Mason et al. |
| 2023/0029639 A1 | 2/2023 | Roy |
| 2023/0047253 A1 | 2/2023 | Gnanasambandam et al. |
| 2023/0048040 A1 | 2/2023 | Hacking et al. |
| 2023/0051751 A1 | 2/2023 | Hacking et al. |
| 2023/0058605 A1 | 2/2023 | Mason |
| 2023/0060039 A1 | 2/2023 | Mason |
| 2023/0072368 A1 | 3/2023 | Mason |
| 2023/0078793 A1 | 3/2023 | Mason |
| 2023/0119461 A1 | 4/2023 | Mason |
| 2023/0190100 A1 | 6/2023 | Stump |
| 2023/0201656 A1 | 6/2023 | Hacking et al. |
| 2023/0207097 A1 | 6/2023 | Mason |
| 2023/0207124 A1 | 6/2023 | Walsh et al. |
| 2023/0215539 A1 | 7/2023 | Rosenberg et al. |
| 2023/0215552 A1 | 7/2023 | Khotilovich et al. |
| 2023/0218950 A1 | 7/2023 | Belson et al. |
| 2023/0245747 A1 | 8/2023 | Rosenberg et al. |
| 2023/0245748 A1 | 8/2023 | Rosenberg et al. |
| 2023/0245750 A1 | 8/2023 | Rosenberg et al. |
| 2023/0245751 A1 | 8/2023 | Rosenberg et al. |
| 2023/0253089 A1 | 8/2023 | Rosenberg et al. |
| 2023/0255555 A1 | 8/2023 | Sundaram et al. |
| 2023/0263428 A1 | 8/2023 | Hull et al. |
| 2023/0274813 A1 | 8/2023 | Rosenberg et al. |
| 2023/0282329 A1 | 9/2023 | Mason et al. |
| 2023/0364472 A1 | 11/2023 | Posnack |
| 2023/0368886 A1 | 11/2023 | Rosenberg |
| 2023/0377710 A1 | 11/2023 | Chen et al. |
| 2023/0377711 A1 | 11/2023 | Rosenberg |
| 2023/0377712 A1 | 11/2023 | Rosenberg |
| 2023/0386639 A1 | 11/2023 | Rosenberg |
| 2023/0395231 A1 | 12/2023 | Rosenberg |
| 2023/0395232 A1 | 12/2023 | Rosenberg |
| 2024/0029856 A1 | 1/2024 | Rosenberg |

FOREIGN PATENT DOCUMENTS

| | | | |
|---|---|---|---|
| CN | 2885238 Y | 4/2007 |
| CN | 101964151 A | 2/2011 |
| CN | 201889024 U | 7/2011 |
| CN | 102670381 A | 9/2012 |
| CN | 103263336 A | 8/2013 |
| CN | 103390357 A | 11/2013 |
| CN | 103473631 A | 12/2013 |
| CN | 103488880 A | 1/2014 |
| CN | 103501328 A | 1/2014 |
| CN | 103721343 A | 4/2014 |
| CN | 203677851 U | 7/2014 |
| CN | 104335211 A | 2/2015 |
| CN | 105683977 A | 6/2016 |
| CN | 103136447 B | 8/2016 |
| CN | 105894088 A | 8/2016 |
| CN | 105930668 A | 9/2016 |
| CN | 205626871 U | 10/2016 |
| CN | 106127646 A | 11/2016 |
| CN | 106236502 A | 12/2016 |
| CN | 106510985 A | 3/2017 |
| CN | 106621195 A | 5/2017 |
| CN | 107066819 A | 8/2017 |
| CN | 107430641 A | 12/2017 |
| CN | 107551475 A | 1/2018 |
| CN | 107736982 A | 2/2018 |
| CN | 107930021 A | 4/2018 |
| CN | 108078737 A | 5/2018 |
| CN | 208224811 A | 12/2018 |
| CN | 109191954 A | 1/2019 |
| CN | 109363887 A | 2/2019 |
| CN | 208573971 U | 3/2019 |
| CN | 110148472 A | 8/2019 |
| CN | 110201358 A | 9/2019 |
| CN | 110215188 A | 9/2019 |
| CN | 110322957 A | 10/2019 |
| CN | 110808092 A | 2/2020 |
| CN | 110931103 A | 3/2020 |
| CN | 110993057 A | 4/2020 |
| CN | 111105859 A | 5/2020 |
| CN | 111111110 A | 5/2020 |
| CN | 111370088 A | 7/2020 |
| CN | 111460305 A | 7/2020 |
| CN | 111790111 A | 10/2020 |
| CN | 112071393 A | 12/2020 |
| CN | 212141371 U | 12/2020 |
| CN | 112289425 A | 1/2021 |
| CN | 212624809 U | 2/2021 |
| CN | 112603295 A | 4/2021 |
| CN | 213190965 U | 5/2021 |
| CN | 113384850 A | 9/2021 |
| CN | 113499572 A | 10/2021 |
| CN | 215136488 U | 12/2021 |
| CN | 113885361 A | 1/2022 |
| CN | 114049961 A | 2/2022 |
| CN | 114203274 A | 3/2022 |
| CN | 216258145 U | 4/2022 |
| CN | 114632302 A | 6/2022 |
| CN | 114694824 A | 7/2022 |
| CN | 114898832 A | 8/2022 |
| CN | 114983760 A | 9/2022 |
| CN | 217472652 U | 9/2022 |
| CN | 110270062 B | 10/2022 |
| CN | 218420859 U | 2/2023 |
| CN | 115954081 A | 4/2023 |
| DE | 102018202497 A1 | 8/2018 |
| DE | 102018211212 A1 | 1/2019 |
| DE | 102019108425 B3 | 8/2020 |
| EP | 0383137 A2 | 8/1990 |
| EP | 0919259 A1 | 6/1999 |
| EP | 1159989 A1 | 12/2001 |
| EP | 1391179 A1 | 2/2004 |
| EP | 1968028 | 9/2008 |
| EP | 2575064 A1 | 4/2013 |
| EP | 1909730 B1 | 4/2014 |
| EP | 2815242 A4 | 12/2014 |
| EP | 2869805 A | 5/2015 |
| EP | 2997951 A1 | 3/2016 |
| EP | 2688472 B1 | 4/2016 |
| EP | 3323473 A1 | 5/2018 |
| EP | 3547322 A1 | 10/2019 |
| EP | 3627514 A1 | 3/2020 |
| EP | 3671700 A1 | 6/2020 |
| EP | 3688537 A1 | 8/2020 |
| EP | 3731733 A1 | 11/2020 |
| EP | 3984508 A1 | 4/2022 |
| EP | 3984509 A1 | 4/2022 |
| EP | 3984510 A1 | 4/2022 |
| EP | 3984511 A1 | 4/2022 |
| EP | 3984512 A1 | 4/2022 |
| EP | 3984513 A1 | 4/2022 |
| EP | 4054699 A1 | 9/2022 |
| EP | 4112033 A1 | 1/2023 |
| FR | 3127393 A1 | 3/2023 |
| GB | 2512431 A | 10/2014 |
| GB | 2591542 B | 3/2022 |
| IN | 201811043670 A | 7/2018 |
| JP | 2000005339 A | 1/2000 |
| JP | 2003225875 A | 8/2003 |
| JP | 2005227928 A | 8/2005 |
| JP | 2005227928 A1 | 8/2005 |
| JP | 2009112336 A | 5/2009 |
| JP | 2013515995 A | 5/2013 |
| JP | 2014104139 A | 6/2014 |
| JP | 3193662 U | 10/2014 |

(56) References Cited

FOREIGN PATENT DOCUMENTS

| | | | |
|---|---|---|---|
| JP | 3198173 U | 6/2015 |
| JP | 5804063 B2 | 11/2015 |
| JP | 6659831 B2 | 10/2017 |
| JP | 2018102842 A | 7/2018 |
| JP | 2019028647 A | 2/2019 |
| JP | 2019134909 A | 8/2019 |
| JP | 6573739 B1 | 9/2019 |
| JP | 2020057082 A | 4/2020 |
| JP | 6710357 B1 | 6/2020 |
| JP | 6775757 B1 | 10/2020 |
| JP | 2021026768 A | 2/2021 |
| JP | 2021027917 A | 2/2021 |
| JP | 6871379 B2 | 5/2021 |
| JP | 2022521378 A | 4/2022 |
| JP | 3238491 U | 7/2022 |
| JP | 7198364 B2 | 12/2022 |
| JP | 7202474 B2 | 1/2023 |
| JP | 7231750 B2 | 3/2023 |
| JP | 7231751 B2 | 3/2023 |
| JP | 7231752 B2 | 3/2023 |
| KR | 20020009724 A | 2/2002 |
| KR | 200276919 Y1 | 5/2002 |
| KR | 20020065253 A | 8/2002 |
| KR | 100582596 B1 | 5/2006 |
| KR | 101042258 B1 | 6/2011 |
| KR | 101258250 B1 | 4/2013 |
| KR | 101325581 B1 | 11/2013 |
| KR | 20140128630 A | 11/2014 |
| KR | 20150017693 A | 2/2015 |
| KR | 20150078191 A | 7/2015 |
| KR | 101580071 B1 | 12/2015 |
| KR | 101647620 B1 | 8/2016 |
| KR | 20160093990 A | 8/2016 |
| KR | 20170038837 A | 4/2017 |
| KR | 20180004928 A | 1/2018 |
| KR | 20190011885 A | 2/2019 |
| KR | 20190029175 A | 3/2019 |
| KR | 101988167 B1 | 6/2019 |
| KR | 102116664 B1 | 7/2019 |
| KR | 101969392 B1 | 8/2019 |
| KR | 102055279 B1 | 12/2019 |
| KR | 102088333 B1 | 3/2020 |
| KR | 102116968 B1 | 3/2020 |
| KR | 20200025290 A | 3/2020 |
| KR | 20200029180 A | 3/2020 |
| KR | 102097190 B1 | 4/2020 |
| KR | 102162522 B1 | 4/2020 |
| KR | 102142713 B1 | 5/2020 |
| KR | 20200056233 A | 5/2020 |
| KR | 102120828 B1 | 6/2020 |
| KR | 102121586 B1 | 6/2020 |
| KR | 20200119665 A | 10/2020 |
| KR | 102173553 B1 | 11/2020 |
| KR | 102180079 B1 | 11/2020 |
| KR | 102224618 B1 | 11/2020 |
| KR | 102188766 B1 | 12/2020 |
| KR | 102196793 B1 | 12/2020 |
| KR | 20210006212 A | 1/2021 |
| KR | 102224188 B1 | 3/2021 |
| KR | 102246049 B1 | 4/2021 |
| KR | 102246050 B1 | 4/2021 |
| KR | 102246051 B1 | 4/2021 |
| KR | 102246052 B1 | 4/2021 |
| KR | 20210052028 A | 5/2021 |
| KR | 102264498 B1 | 6/2021 |
| KR | 102352602 B1 | 1/2022 |
| KR | 102352603 B1 | 1/2022 |
| KR | 102352604 B1 | 1/2022 |
| KR | 20220004639 A | 1/2022 |
| KR | 102387577 B1 | 4/2022 |
| KR | 102421437 B1 | 7/2022 |
| KR | 20220102207 A | 7/2022 |
| KR | 102427545 B1 | 8/2022 |
| KR | 102467495 B1 | 11/2022 |
| KR | 102467496 B1 | 11/2022 |
| KR | 102469723 B1 | 11/2022 |
| KR | 102471990 B1 | 11/2022 |
| KR | 20220145989 A | 11/2022 |
| KR | 20220156134 A | 11/2022 |
| KR | 102502744 B1 | 2/2023 |
| KR | 20230019349 A | 2/2023 |
| KR | 20230019350 A | 2/2023 |
| KR | 20230026556 A | 2/2023 |
| KR | 20230026668 A | 2/2023 |
| KR | 20230040526 | 3/2023 |
| KR | 20230050506 A | 4/2023 |
| KR | 20230056118 A | 4/2023 |
| KR | 102528503 B1 | 5/2023 |
| KR | 102531930 B1 | 5/2023 |
| KR | 102532766 B1 | 5/2023 |
| KR | 102539190 B1 | 6/2023 |
| NO | 2022212921 A1 | 10/2022 |
| RU | 2014131288 A | 2/2016 |
| RU | 2607953 C2 | 1/2017 |
| TW | M474545 U | 3/2014 |
| TW | M638437 U | 3/2023 |
| WO | 0149235 A2 | 7/2001 |
| WO | 0151083 A2 | 7/2001 |
| WO | 2001050387 A1 | 7/2001 |
| WO | 2001056465 A1 | 8/2001 |
| WO | 02062211 A2 | 8/2002 |
| WO | 02093312 A2 | 11/2002 |
| WO | 2003043494 | 5/2003 |
| WO | 2005018453 A1 | 3/2005 |
| WO | 2006004430 A2 | 1/2006 |
| WO | 2007102709 A1 | 9/2007 |
| WO | 2008114291 A1 | 9/2008 |
| WO | 2009003170 A1 | 12/2008 |
| WO | 2009008968 A1 | 1/2009 |
| WO | 2011025322 A2 | 3/2011 |
| WO | 2012128801 A1 | 9/2012 |
| WO | 2013002568 A2 | 1/2013 |
| WO | 2023164292 A1 | 3/2013 |
| WO | 2013122839 A1 | 8/2013 |
| WO | 2014011447 A1 | 1/2014 |
| WO | 2014163976 A1 | 10/2014 |
| WO | 2015026744 A1 | 2/2015 |
| WO | 2015065298 A1 | 5/2015 |
| WO | 2015082555 A1 | 6/2015 |
| WO | 2016151364 A1 | 9/2016 |
| WO | 2016154318 A1 | 9/2016 |
| WO | 2017030781 A1 | 2/2017 |
| WO | 2017166074 A1 | 5/2017 |
| WO | 2017091691 A1 | 6/2017 |
| WO | 2017165238 A1 | 9/2017 |
| WO | 2018081795 A1 | 5/2018 |
| WO | 2018171853 A1 | 9/2018 |
| WO | 2019022706 A1 | 1/2019 |
| WO | 2019204876 A1 | 4/2019 |
| WO | 2019143940 A1 | 7/2019 |
| WO | 2020185769 A1 | 3/2020 |
| WO | 2020075190 A1 | 4/2020 |
| WO | 2020130979 A1 | 6/2020 |
| WO | 2020149815 A2 | 7/2020 |
| WO | 2020229705 A1 | 11/2020 |
| WO | 2020245727 A1 | 12/2020 |
| WO | 2020249855 A1 | 12/2020 |
| WO | 2020252599 A1 | 12/2020 |
| WO | 2020256577 A1 | 12/2020 |
| WO | 2021021447 A1 | 2/2021 |
| WO | 2021022003 A1 | 2/2021 |
| WO | 2021038980 A1 | 3/2021 |
| WO | 2021055427 A1 | 3/2021 |
| WO | 2021055491 A1 | 3/2021 |
| WO | 2021061061 A1 | 4/2021 |
| WO | 2021081094 A1 | 4/2021 |
| WO | 2021090267 A1 | 5/2021 |
| WO | 2021138620 A1 | 7/2021 |
| WO | 2021216881 A1 | 10/2021 |
| WO | 2021236542 A1 | 11/2021 |
| WO | 2021236961 A1 | 11/2021 |
| WO | 2021262809 A1 | 12/2021 |
| WO | 2022047006 A1 | 3/2022 |
| WO | 2022092493 A1 | 5/2022 |

(56) References Cited

FOREIGN PATENT DOCUMENTS

| | | | |
|---|---|---|---|
| WO | 2022092494 | A1 | 5/2022 |
| WO | 2022212883 | A1 | 10/2022 |
| WO | 2022216498 | A1 | 10/2022 |
| WO | 2022251420 | A1 | 12/2022 |
| WO | 2023008680 | A1 | 2/2023 |
| WO | 2023008681 | A1 | 2/2023 |
| WO | 2023022319 | A1 | 2/2023 |
| WO | 2023022320 | A1 | 2/2023 |
| WO | 2023052695 | A1 | 4/2023 |
| WO | 2023091496 | A1 | 5/2023 |
| WO | 2023215155 | A1 | 11/2023 |
| WO | 2023230075 | A1 | 11/2023 |
| WO | 2024013267 | A1 | 1/2024 |
| WO | 2024107807 | A1 | 5/2024 |

OTHER PUBLICATIONS

Natalie Tornese, "Medical Coding for Treadmill Stress Testing—An Overview," https://www.outsourcestrategies.com/blog/medical-coding-for-treadmill-stress-testing-an-overview/. (Year: 2015).*

Jeong et al., "Remotely controlled biking is associated with improved adherence to prescribed cycling speed," Technology and Health Care 23 (2015) S543-S549; DOI 10.3233/THC-150992. (Year: 2015).*

Lausten et al., "Telemonitored exercise-based cardiac rehabilitation improves physical capacity and health-related quality of life," Journal of Telemedicine and Telecare, 2020, vol. 26(1-2) 36-44; DOI: 10.1177/1357633X18792808 journals.sagepub.com/home/jtt. (Year: 2020).*

Jennifer Bresnick, "What is the Role of Natural Language Processing in Healthcare?", pp. 1-7, published Aug. 18, 2016, retrieved on Feb. 1, 2022 from https://healthitanalytics.com/ featu res/what-is-the-role-of-natural-language-processing-in-healthcare.

Alex Bellec, "Part-of-Speech tagging tutorial with the Keras Deep Learning library," pp. 1-16, published Mar. 27, 2018, retrieved on Feb. 1, 2022 from https://becominghuman.ai/part-of-speech-tagging-tutorial-with-the-keras-deep-learning-library-d7f93fa05537.

Kavita Ganesan, All you need to know about text preprocessing for NLP and Machine Learning, pp. 1-14, published Feb. 23, 2019, retrieved on Feb. 1, 2022 from https:// towardsdatascience.com/all-you-need-to-know-about-text-preprocessing-for-nlp-and-machine-learning-bcl c5765ff67.

Badreesh Shetty, "Natural Language Processing (NPL) for Machine Learning," pp. 1-13, published Nov. 24, 2018, retrieved on Feb. 1, 2022 from https://towardsdatascience. com/natural-language-processing-nlp-for-machine-learning-d44498845d5b.

Malloy, Online Article "AI-enabled EKGs find difference between numerical age and biological age significantly affects health, longevity", Website: https://newsnetwork.mayoclinic.org/discussion/ai-enabled-ekgs-find-difference-between-numerical-age-and-biological-age-significantly-affects-health-longevity/, Mayo Clinic News Network, May 20, 2021, retrieved: Jan. 23, 2023, p. 1-4.

Barrett et al., "Artificial intelligence supported patient self-care in chronic heart failure: a paradigm shift from reactive to predictive, preventive and personalised care," EPMA Journal (2019), pp. 445-464.

Oerkild et al., "Home-based cardiac rehabilitation is an attractive alternative to No. cardiac rehabilitation for elderly patients with coronary heart disease: results from a randomised clinical trial," BMJ Open Accessible Medical Research, Nov. 22, 2012, pp. 1-9.

Bravo-Escobar et al., "Effectiveness and safety of a home-based cardiac rehabilitation programme of mixed surveillance in patients with ischemic heart disease at moderate cardiovascular risk: A randomised, controlled clinical trial," BMC Cardiovascular Disorders, 2017, pp. 1-11, vol. 17:66.

Thomas et al., "Home-Based Cardiac Rehabilitation," Circulation, 2019, pp. e69-e89, vol. 140.

Thomas et al., "Home-Based Cardiac Rehabilitation," Journal of the American College of Cardiology, Nov. 1, 2019, pp. 133-153, vol. 74.

Thomas et al., "Home-Based Cardiac Rehabilitation," HHS Public Access, Oct. 2, 2020, pp. 1-39.

Dittus et al., "Exercise-Based Oncology Rehabilitation: Leveraging the Cardiac Rehabilitation Model," Journal of Cardiopulmonary Rehabilitation and Prevention, 2015, pp. 130-139, vol. 35.

Chen et al., "Home-based cardiac rehabilitation improves quality of life, aerobic capacity, and readmission rates in patients with chronic heart failure," Medicine, 2018, pp. 1-5 vol. 97:4.

Lima de Melo Ghisi et al., "A systematic review of patient education in cardiac patients: Do they increase knowledge and promote health behavior change?," Patient Education and Counseling, 2014, pp. 1-15.

Fang et al., "Use of Outpatient Cardiac Rehabilitation Among Heart Attack Survivors—20 States and the District of Columbia, 2013 and Four States, 2015," Morbidity and Mortality Weekly Report, vol. 66, No. 33, Aug. 25, 2017, pp. 869-873.

Beene et al., "AI and Care Delivery: Emerging Opportunities for Artificial Intelligence to Transform How Care is Delivered," Nov. 2019, American Hospital Association, pp. 1-12.

Gerbild et al., "Physical Activity to Improve Erectile Dysfunction: A Systematic Review of Intervention Studies," Sexual Medicine, 2018, 15 pages.

Davenport et al., "The Potential For Artificial Intelligence In Healthcare", 2019, Future Healthcare Journal 2019, vol. 6, No. 2: Year: 2019, pp. 1-5.

Ahmed et al., "Artificial Intelligence With Multi-Functional Machine Learning Platform Development for Better Healthcare and Precision Medicine", 2020, Database (Oxford), 2020:baaa010. doi: 10.1093/database/baaa010 (Year: 2020), pp. 1-35.

Ruiz Ivan et al., "Towards a physical rehabilitation system using a telemedicine approach", Computer Methods in Biomechanics and Biomedical Engineering: Imaging & Visualization, vol. 8, No. 6, Jul. 28, 2020, pp. 671-680, XP055914810.

De Canniere Helene et al., "Wearable Monitoring and Interpretable Machine Learning Can Objectively Track Progression in Patients during Cardiac Rehabilitation", Sensors, vol. 20, No. 12, Jun. 26, 2020, XP055914617, pp. 1-15.

Boulanger Pierre et al., "A Low-cost Virtual Reality Bike for Remote Cardiac Rehabilitation", Dec. 7, 2017, Advances in Biometrics: International Conference, ICB 2007, Seoul, Korea, pp. 155-166.

Yin Chieh et al., "A Virtual Reality-Cycling Training System for Lower Limb Balance Improvement", BioMed Research International, vol. 2016, pp. 1-10.

Website for "Pedal Exerciser", p. 1, retrieved on Sep. 9, 2022 from https://www.vivehealth.com/collections/physical-therapy-equipment/products/pedalexerciser.

Website for "Functional Knee Brace with ROM", p. 1, retrieved on Sep. 9, 2022 from http://medicalbrace.gr/en/product/functional-knee-brace-with-goniometer-mbtelescopicknee/.

Website for "ComfySplints Goniometer Knee", pp. 1-5, retrieved on Sep. 9, 2022 from https://www.comfysplints.com/product/knee-splints/.

Website for "BMI FlexEze Knee Corrective Orthosis (KCO)", pp. 1-4, retrieved on Sep. 9, 2022 from https://orthobmi.com/products/bmi-flexeze%C2%AE-knee-corrective-orthosis-kco.

Website for "Neoprene Knee Brace with goniometer—Patella ROM MB.4070", pp. 1-4, retrieved on Sep. 9, 2022 from https://www.fortuna.com.gr/en/product/neoprene-knee-brace-with-goniometer-patella-rom-mb-4070/.

Kuiken et al., "Computerized Biofeedback Knee Goniometer: Acceptance and Effect on Exercise Behavior in Post-total Knee Arthroplasty Rehabilitation," Biomedical Engineering Faculty Research and Publications, 2004, pp. 1-10.

Ahmed et al., "Artificial intelligence with multi-functional machine learning platform development for better healthcare and precision medicine," Database, 2020, pp. 1-35.

Davenport et al., "The potential for artificial intelligence in healthcare," Digital Technology, Future Healthcare Journal, 2019, pp. 1-5, vol. 6, No. 2.

(56) References Cited

OTHER PUBLICATIONS

Website for "OxeFit XS1", pp. 1-3, retrieved on Sep. 9, 2022 from https://www.oxefit.com/xs1.
Website for "Preva Mobile", pp. 1-6, retrieved on Sep. 9, 2022 from https://www.precor.com/en-us/resources/introducing-preva-mobile.
Website for "J-Bike", pp. 1-3, retrieved on Sep. 9, 2022 from https://www.magneticdays.com/en/cycling-for-physical-rehabilitation.
Website for "Excy", pp. 1-12, retrieved on Sep. 9, 2022 from https://excy.com/portable-exercise-rehabilitation-excy-xcs-pro/.
Website for "OxeFit XP1", p. 1, retrieved on Sep. 9, 2022 from https://www.oxefit.com/xp1.
International Search Report and Written Opinion for International Application No. PCT/US2021/032807, Date of Mailing Sep. 6, 2021, 11 pages.
Jeong et al., "Computer-assisted upper extremity training using interactive biking exercise (iBikE) platform," Sep. 2012, pp. 1-5, 34th Annual International Conference of the IEEE EMBS.
Alcaraz et al., "Machine Learning as Digital Therapy Assessment for Mobile Gait Rehabilitation," 2018 IEEE 28th International Workshop on Machine Learning for Signal Processing (MLSP), Aalborg, Denmark, 2018, 6 pages.
Androutsou et al., "A Smartphone Application Designed to Engage the Elderly in Home-Based Rehabilitation," Frontiers in Digital Health, Sep. 2020, vol. 2, Article 15, 13 pages.
Silva et al., "SapoFitness: A mobile health application for dietary evaluation," 2011 IEEE 13th International Conference on U e-Health Networking, Applications and Services, Columbia, MO, USA, 2011, 6 pages.
Wang et al., "Interactive wearable systems for upper body rehabilitation: a systematic review," Journal of NeuroEngineering and Rehabilitation, 2017, 21 pages.
Marzolini et al., "Eligibility, Enrollment, and Completion of Exercise-Based Cardiac Rehabilitation Following Stroke Rehabilitation: What Are the Barriers?," Physical Therapy, vol. 100, No. 1, 2019, 13 pages.
Nijjar et al., "Randomized Trial of Mindfulness-Based Stress Reduction in Cardiac Patients Eligible for Cardiac Rehabilitation," Scientific Reports, 2019, 12 pages.
Lara et al., "Human-Robot Sensor Interface for Cardiac Rehabilitation," IEEE International Conference on Rehabilitation Robotics, Jul. 2017, 8 pages.
Ishraque et al., "Artificial Intelligence-Based Rehabilitation Therapy Exercise Recommendation System," 2018 IEEE MIT Undergraduate Research Technology Conference (URTC), Cambridge, MA, USA, 2018, 5 pages.
Zakari et al., "Are There Limitations to Exercise Benefits in Peripheral Arterial Disease?," Frontiers in Cardiovascular Medicine, Nov. 2018, vol. 5, Article 173, 12 pages.
You et al., "Including Blood Vasculature into a Game-Theoretic Model of Cancer Dynamics," Games 2019, 10, 13, 22 pages.
Jeong et al., "Computer-assisted upper extremity training using interactive biking exercise (iBikE) platform," Sep. 2012, 34th Annual International Conference of the IEEE EMBS, 5 pages.
International Search Report and Written Opinion for PCT/US2023/014137, dated Jun. 9, 2023, 13 pages.
Website for "Esino 2022 Physical Therapy Equipments Arm Fitness Indoor Trainer Leg Spin Cycle Machine Exercise Bike for Elderly," https://www.made-in-china.com/showroom/esinogroup/product-detailYdZtwGhCMKVR/China-Esino-2022-Physical-Therapy-Equipments-Arm-Fitness-Indoor-Trainer-Leg-Spin-Cycle-Machine-Exercise-Bike-for-Elderly.html, retrieved on Aug. 29, 2023, 5 pages.
Abedtash, "An Interoperable Electronic Medical Record-Based Platform For Personalized Predictive Analytics", ProQuest LLC, Jul. 2017, 185 pages.
Chrif et al., "Control design for a lower-limb paediatric therapy device using linear motor technology," Article, 2017, pp. 119-127, Science Direct, Switzerland.
Robben et al., "Delta Features From Ambient Sensor Data are Good Predictors of Change in Functional Health," Article, 2016, pp. 2168-2194, vol. 21, No. 4, IEEE Journal of Biomedical and Health Informatics.
Kantoch et al., "Recognition of Sedentary Behavior by Machine Learning Analysis of Wearable Sensors during Activities of Daily Living for Telemedical Assessment of Cardiovascular Risk," Article, 2018, 17 pages, Sensors, Poland.
Warburton et al., "International Launch of the PAR-•Q+ and ePARmed-•X+ Validation of the PAR-•Q+ and ePARmed••X+," Health & Fitness Journal of Canada, 2011, 9 pages, vol. 4, No. 2.
Jeong et al., "Remotely controlled biking is associated with improved adherence to prescribed cycling speed," Technology and Health Care 23, 2015, 7 pages.
Laustsen et al., "Telemonitored exercise-based cardiac rehabilitation improves physical capacity and health-related quality of life," Journal of Telemedicine and Telecare, 2020, DOI: 10.1177/1357633X18792808, 9 pages.
Blasiak et al., "curate.ai: Optimizing Personalized Medicine with Artificial Intelligence," Slas Technology: Translating Life Sciences Innovation, 2020, 11 pages.
Ahmed et al., "Artificial Intelligence With Multi-Functional Machine Learning Platform Development for Better Healthcare and Precision Medicine," Database (Oxford), 2020, pp. 1-35, vol. 2020.
Davenport et al., "The Potential for Artificial Intelligence in Healthcare," Future Healthcare Journal, 2019, pp. 94-98, vol. 6, No. 2.

\* cited by examiner

SYSTEM AND METHOD FOR PROCESSING MEDICAL CLAIMS

CROSS-REFERENCES TO RELATED APPLICATIONS

This application is a continuation-in-part of U.S. patent application Ser. No. 17/021,895, filed Sep. 15, 2020, titled "Telemedicine for Orthopedic Treatment," which claims priority to and the benefit of U.S. Provisional Patent Application Ser. No. 62/910,232, filed Oct. 3, 2019, titled "Telemedicine for Orthopedic Treatment," the entire disclosures of which are hereby incorporated by reference for all purposes. This application also claims priority to and the benefit of U.S. Provisional Patent Application Ser. No. 63/028,392, filed May 21, 2020, titled "System and Method for Processing Medical Claims," the entire disclosure of which is hereby incorporated by reference for all purposes.

TECHNICAL FIELD

This disclosure relates generally to systems and methods for adjudication of medical device claims.

BACKGROUND

Electronic medical record (EMR) systems may be used to generate and maintain an electronic record of health-related information relating to or about individuals within a health care organization. The health-related information may be input by a variety of entities, e.g., the individuals' health care providers, where such entries may be made by any medically-related entity or its representatives, for example: administrators, nurses, doctors, or other authorized individuals; insurance companies; billing companies; hospitals; testing centers, such as those related to radiologic services, blood and bodily fluid testing services; and psychological service providers, such as psychologists, social workers, addiction and other counselors, and psychiatrists. Each healthcare service may have one or more medical billing codes, for example Diagnosis-Related Group (DRG) and/or International Classification of Diseases (ICD) codes, e.g., ICD-10, assigned for billing purposes. Some of the individual's EMRs, including the one or more medical billing codes, may be transferred to a third-party payor, such as an insurance company, for invoicing the individual's medical claims for the individual's healthcare services. A medical claim, or a claim, is a medical bill, or bill, submitted to a health insurance carrier, or other party responsible for payment, for services rendered and/or goods provided to patients by health care providers. After a medical claim is submitted to the insurance company, the insurance company determines its financial responsibility for the payment to the healthcare provider (i.e., claim adjudication). The insurance company may have procedures to ensure that no false medical claims are approved for payment, for example, by rejecting payment for medical billing codes inconsistent with the healthcare services provided. As a result of such procedures, the insurance company may decide to pay the medical claim in full, reduce the medical bill, deny the full medical claim, or revise the nature of the claim such that it becomes eligible for full or partial payment.

Medical billing may present difficulties in medical billing code adjudication, often making it difficult for the healthcare provider to be paid for its healthcare services. The data transfer from the healthcare provider to the insurance company may not always be reliable, due in part to the volume of data, data security, and data consistency issues (i.e., errors in the information). Further, human error or malicious interlopers can reduce the reliability of such systems. The use of telemedicine may result in additional risks related to fraud, waste, and abuse, risks which bad actors can exploit. For example, if, at a location other than a healthcare facility, the medical device is being used, a healthcare provider may not oversee the use (e.g., treatment, rehabilitation, or testing), and therefore, the healthcare provider may not be able to easily confirm or validate the accuracy of the medical billing Further, mass transfer of this data as data packets between various parts of the systems may increase network loads and slow processing time.

SUMMARY

In general, the present disclosure provides a system and methods for processing medical claims based on medical services. Such medical services may have been performed by an individual, by a medical device, or by combinations thereof, e.g., individuals using certain medical devices.

An aspect of the disclosed embodiments includes a computer-implemented system for processing medical claims. The computer-implemented system includes a medical device configured to be manipulated by a user while the user performs a treatment plan; a patient interface associated with the medical device, the patient interface comprising an output configured to present telemedicine information associated with a telemedicine session; and a processor. During the telemedicine session, the processor is configured to receive information from a medical device. Using the device-generated information, the processor is further configured to determine device-based medical coding information. The processor is further configured to transmit the device-based medical coding information to a claim adjudication server.

An aspect of the disclosed embodiments includes a system for processing medical claims. The system includes a processor configured to receive device-generated information from a medical device. Using the device-generated information received, the processor is configured to determine device-based medical coding information. The processor is further configured to transmit the device-based medical coding information to a claim adjudication server.

An aspect of the disclosed embodiments includes a method for a clinic server to process medical claims. The method includes receiving information from a medical device. The method further includes, using the device-generated information, determining device-based medical coding information. The method further includes transmitting the device-based medical coding information to a claim adjudication server.

An aspect of the disclosed embodiments includes a tangible, non-transitory computer-readable medium. The tangible, non-transitory computer-readable medium stores instructions that, when executed, cause a processor to receive device-generated information from a medical device. Using the device-generated information received, the processor determines device-based medical coding information. The processor further transmits the device-based medical coding information to a claim adjudication server.

In yet another aspect, a system for generating and processing medical billing codes is disclosed. The system includes a medical device and a computing device. The computing device comprises a processor in communication with the medical device. The processor is configured to receive information from the medical device and transmit the device-generated information to a clinic server. Using the device-generated information received, the processor is configured to determine device-based medical coding information. The processor is further configured to cause the clinic server to transmit the device-based medical coding information to a claim adjudication server.

An aspect of the disclosed embodiments includes a method for operating a medical device. The method includes receiving information from the medical device. The method further includes transmitting the device-generated information to the clinic server. Using the device-generated information received, the method further includes causing the clinic server to determine device-based medical coding information. The method further includes causing the clinic server to transmit the device-based medical coding information to a claim adjudication server.

An aspect of the disclosed embodiments includes a tangible, non-transitory computer-readable medium. The tangible, non-transitory computer-readable medium stores instructions that, when executed, cause a processor to receive information from the medical device. The instructions further cause the processor to transmit the device-generated information to a clinic server. The instructions further cause the processor to cause the clinic server to, using the device-generated information, determine device-based medical coding information. The instructions further cause the processor to cause the clinic server to transmit the device-based medical coding information to a claim adjudication server.

Other technical features may be readily apparent to one skilled in the art from the following figures, descriptions, and claims.

Another aspect of the disclosed embodiments includes a system that includes a processing device and a memory communicatively coupled to the processing device and capable of storing instructions. The processing device executes the instructions to perform any of the methods, operations, or steps described herein.

Another aspect of the disclosed embodiments includes a tangible, non-transitory computer-readable medium storing instructions that, when executed, cause a processing device to perform any of the methods, operations, or steps disclosed herein.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

For a more complete understanding of this disclosure and its advantages, reference is now made to the following description, taken in conjunction with the accompanying drawings, in which.

NOTATION AND NOMENCLATURE

Figure 1:
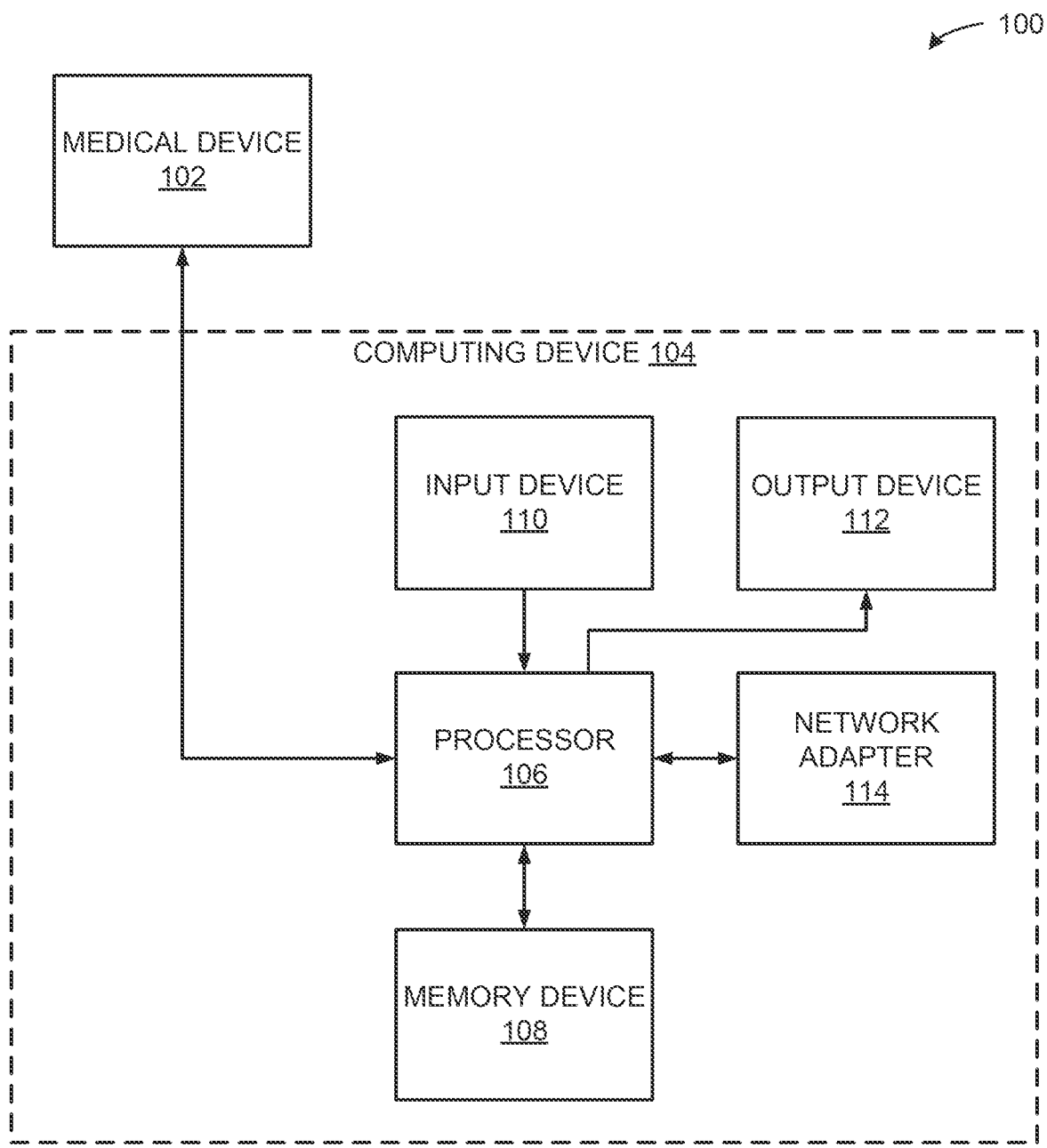
FIG. 1 generally illustrates a component diagram of an illustrative medical system according to the principles of the present disclosure.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," "inside," "outside," "contained within," "superimposing upon," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

A "treatment plan" may include one or more treatment protocols, and each treatment protocol includes one or more treatment sessions. Each treatment session comprises several session periods, with each session period including a particular exercise for treating the body part of the patient. For example, a treatment plan for post-operative rehabilitation after a knee surgery may include an initial treatment protocol with twice daily stretching sessions for the first 3 days after surgery and a more intensive treatment protocol with active exercise sessions performed 4 times per day starting 4 days after surgery. A treatment plan may also include information pertaining to a medical procedure to perform on the patient, a treatment protocol for the patient using a treatment device, a diet regimen for the patient, a medication regimen for the patient, a sleep regimen for the patient, additional regimens, or some combination thereof.

The terms telemedicine, telehealth, telemed, teletherapeutic, telemedicine, remote medicine, etc. may be used interchangeably herein.

The term "optimal treatment plan" may refer to optimizing a treatment plan based on a certain parameter or factors or combinations of more than one parameter or factor, such as, but not limited to, a measure of benefit which one or more exercise regimens provide to users, one or more probabilities of users complying with one or more exercise regimens, an amount, quality or other measure of sleep associated with the user, information pertaining to a diet of the user, information pertaining to an eating schedule of the user, information pertaining to an age of the user, information pertaining to a sex of the user, information pertaining to a gender of the user, an indication of a mental state of the user, information pertaining to a genetic condition of the user, information pertaining to a disease state of the user, an indication of an energy level of the user, information pertaining to a microbiome from one or more locations on or in the user (e.g., skin, scalp, digestive tract, vascular system, etc.), or some combination thereof.

As used herein, the term healthcare provider may include a medical professional (e.g., such as a doctor, a nurse, a therapist, and the like), an exercise professional (e.g., such as a coach, a trainer, a nutritionist, and the like), or another professional sharing at least one of medical and exercise attributes (e.g., such as an exercise physiologist, a physical therapist, an occupational therapist, and the like). As used herein, and without limiting the foregoing, a "healthcare provider" may be a human being, a robot, a virtual assistant, a virtual assistant in virtual and/or augmented reality, or an artificially intelligent entity, such entity including a software program, integrated software and hardware, or hardware alone.

Real-time may refer to less than or equal to 2 seconds. Near real-time may refer to any interaction of a sufficiently short time to enable two individuals to engage in a dialogue via such user interface, and will preferably but not determinatively be less than 10 seconds (or any suitably proximate difference between two different times) but greater than 2 seconds.

Any of the systems and methods described in this disclosure may be used in connection with rehabilitation. Rehabilitation may be directed at cardiac rehabilitation, rehabilitation from stroke, multiple sclerosis, Parkinson's disease, myasthenia gravis, Alzheimer's disease, any other neurodegenative or neuromuscular disease, a brain injury, a spinal cord injury, a spinal cord disease, a joint injury, a joint disease, post-surgical recovery, or the like. Rehabilitation can further involve muscular contraction in order to improve blood flow and lymphatic flow, engage the brain and nervous system to control and affect a traumatized area to increase the speed of healing, reverse or reduce pain (including arthralgias and myalgias), reverse or reduce stiffness, recover range of motion, encourage cardiovascular engagement to stimulate the release of pain-blocking hormones or to encourage highly oxygenated blood flow to aid in an overall feeling of well-being. Rehabilitation may be provided for individuals of average weight in reasonably good physical condition having no substantial deformities, as well as for individuals more typically in need of rehabilitation, such as those who are elderly, obese, subject to disease processes, injured and/or who have a severely limited range of motion. Unless expressly stated otherwise, is to be understood that rehabilitation includes prehabilitation (also referred to as "pre-habilitation" or "prehab"). Prehabilitation may be used as a preventative procedure or as a pre-surgical or pre-treatment procedure. Prehabilitation may include any action performed by or on a patient (or directed to be performed by or on a patient, including, without limitation, remotely or distally through telemedicine) to, without limitation, prevent or reduce a likelihood of injury (e.g., prior to the occurrence of the injury); improve recovery time subsequent to surgery; improve strength subsequent to surgery; or any of the foregoing with respect to any non-surgical clinical treatment plan to be undertaken for the purpose of ameliorating or mitigating injury, dysfunction, or other negative consequence of surgical or non-surgical treatment on any external or internal part of a patient's body. For example, a mastectomy may require prehabilitation to strengthen muscles or muscle groups affected directly or indirectly by the mastectomy. As a further non-limiting example, the removal of an intestinal tumor, the repair of a hernia, open-heart surgery or other procedures performed on internal organs or structures, whether to repair those organs or structures, to excise them or parts of them, to treat them, etc., can require cutting through, dissecting and/or harming numerous muscles and muscle groups in or about, without limitation, the skull or face, the abdomen, the ribs and/or the thoracic cavity, as well as in or about all joints and appendages. Prehabilitation can improve a patient's speed of recovery, measure of quality of life, level of pain, etc. in all the foregoing procedures. In one embodiment of prehabilitation, a pre-surgical procedure or a pre-non-surgical-treatment may include one or more sets of exercises for a patient to perform prior to such procedure or treatment. Performance of the one or more sets of exercises may be required in order to qualify for an elective surgery, such as a knee replacement. The patient may prepare an area of his or her body for the surgical procedure by performing the one or more sets of exercises, thereby strengthening muscle groups, improving existing muscle memory, reducing pain, reducing stiffness, establishing new muscle memory, enhancing mobility (i.e., improve range of motion), improving blood flow, and/or the like.

The phrase, and all permutations of the phrase, "respective measure of benefit with which one or more exercise regimens may provide the user" (e.g., "measure of benefit," "respective measures of benefit," "measures of benefit," "measure of exercise regimen benefit," "exercise regimen benefit measurement," etc.) may refer to one or more measures of benefit with which one or more exercise regimens may provide the user.

DETAILED DESCRIPTION

The following discussion is directed to various embodiments of the present disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Determining optimal remote examination procedures to create an optimal treatment plan for a patient having certain characteristics (e.g., vital-sign or other measurements; performance; demographic; psychographic; geographic; diagnostic; measurement- or test-based; medically historic; behavioral historic; cognitive; etiologic; cohort-associative; differentially diagnostic; surgical, physically therapeutic, pharmacologic and other treatment(s) recommended; etc.) may be a technically challenging problem. For example, a multitude of information may be considered when determining a treatment plan, which may result in inefficiencies and inaccuracies in the treatment plan selection process. In a rehabilitative setting, some of the multitude of information considered may include characteristics of the patient such as personal information, performance information, and measurement information. The personal information may include, e.g., demographic, psychographic or other information, such as an age, a weight, a gender, a height, a body mass index, a medical condition, a familial medication history, an injury, a medical procedure, a medication prescribed, or some combination thereof. The performance information may include, e.g., an elapsed time of using a treatment device, an amount of force exerted on a portion of the treatment device, a range of motion achieved on the treatment device, a movement speed of a portion of the treatment device, a duration of use of the treatment device, an indication of a plurality of pain levels using the treatment device, or some combination thereof. The measurement information may include, e.g., a vital sign, a respiration rate, a heartrate, a temperature, a blood pressure, a glucose level or other biomarker, or some combination thereof. It may be desirable to process and analyze the characteristics of a multitude of patients, the treatment plans performed for those patients, and the results of the treatment plans for those patients.

Further, another technical problem may involve distally treating, via a computing device during a telemedicine session, a patient from a location different than a location at which the patient is located. An additional technical problem is controlling or enabling, from the different location, the control of a treatment device used by the patient at the patient's location. Oftentimes, when a patient undergoes rehabilitative surgery (e.g., knee surgery), a medical professional may prescribe a treatment device to the patient to use to perform a treatment protocol at their residence or at any mobile location or temporary domicile. A medical professional may refer to a doctor, physician assistant, nurse, chiropractor, dentist, physical therapist, acupuncturist, physical trainer, or the like. A medical professional may refer to any person with a credential, license, degree, or the like in the field of medicine, physical therapy, rehabilitation, or the like.

When the healthcare provider is located in a location different from the patient and the treatment device, it may be technically challenging for the healthcare provider to monitor the patient's actual progress (as opposed to relying on the patient's word about their progress) in using the treatment device, modify the treatment plan according to the patient's progress, adapt the treatment device to the personal characteristics of the patient as the patient performs the treatment plan, and the like.

Further, in addition to the information described above, determining optimal examination procedures for a particular ailment (e.g., injury, disease, any applicable medical condition, etc.) may include physically examining the injured body part of a patient. The healthcare provider, such as a physician or a physical therapist, may visually inspect the injured body part (e.g., a knee joint). The inspection may include looking for signs of inflammation or injury (e.g., swelling, redness, and warmth), deformity (e.g., symmetrical joints and abnormal contours and/or appearance), or any other suitable observation. To determine limitations of the injured body part, the healthcare provider may observe the injured body part as the patient attempts to perform normal activity (e.g., bending and extending the knee and gauging any limitations to the range of motion of the injured knee). The healthcare provide may use one or more hands and/or fingers to touch the injured body part. By applying pressure to the injured body part, the healthcare provider can obtain information pertaining to the extent of the injury. For example, the healthcare provider's fingers may palpate the injured body part to determine if there is point tenderness, warmth, weakness, strength, or to make any other suitable observation.

It may be desirable to compare characteristics of the injured body part with characteristics of a corresponding non-injured body part to determine what an optimal treatment plan for the patient may be such that the patient can obtain a desired result. Thus, the healthcare provider may examine a corresponding non-injured body part of the patient. For example, the healthcare provider's fingers may palpate a non-injured body part (e.g., a left knee) to determine a baseline of how the patient's non-injured body part feels and functions. The healthcare provider may use the results of the examination of the non-injured body part to determine the extent of the injury to the corresponding injured body part (e.g., a right knee). Additionally, injured body parts may affect other body parts (e.g., a knee injury may limit the use of the affected leg, leading to atrophy of leg muscles). Thus, the healthcare provider may also examine additional body parts of the patient for evidence of atrophy of or injury to surrounding ligaments, tendons, bones, and muscles, examples of muscles being such as quadriceps, hamstrings, or calf muscle groups of the leg with the knee injury. The healthcare provider may also obtain information as to a pain level of the patient before, during, and/or after the examination.

The healthcare provider can use the information obtained from the examination (e.g., the results of the examination) to determine a proper treatment plan for the patient. If the healthcare provider cannot conduct a physical examination of the one or more body parts of the patient, the healthcare provider may not be able to fully assess the patient's injury and the treatment plan may not be optimal. Accordingly, embodiments of the present disclosure pertain to systems and methods for conducting a remote examination of a patient. The remote examination system provides the healthcare provider with the ability to conduct a remote examination of the patient, not only by communicating with the patient, but by virtually observing and/or feeling the patient's one or more body parts.

In some embodiments, the systems and methods described herein may be configured for manipulation of a medical device. For example, the systems and methods may be configured to use a medical device configured to be manipulated by an individual while the individual is performing a treatment plan. The individual may include a user, patient, or other a person using the treatment device to perform various exercises for prehabilitation, rehabilitation, stretch training, e.g., pliability, medical procedures, and the like. The systems and methods described herein may be configured to use and/or provide a patient interface comprising an output device, wherein the output device is configured to present telemedicine information associated with a telemedicine session.

In some embodiments, the systems and methods described herein may be configured for processing medical claims. For example, the system includes a processor configured to receive device-generated information from a medical device. Using the device-generated information received, the processor is configured to determine device-based medical coding information. The processor is further configured to transmit the device-based medical coding information to a claim adjudication server. Any or all of the methods described may be implemented during a telemedicine session or at any other desired time.

In some embodiments, the medical claims may be processed, during a telemedicine or telehealth session, by a healthcare provider. The healthcare provider may select a particular treatment plan for the patient to cause that treatment plan to be transmitted to the patient and/or to control, based on the treatment plan, the treatment device. In some embodiments, to facilitate telehealth or telemedicine applications, including remote diagnoses, determination of treatment plans and rehabilitative and/or pharmacologic prescriptions, the artificial intelligence engine may receive data, instructions, or the like and/or operate distally from the patient and the treatment device.

In such cases, the recommended treatment plans and/or excluded treatment plans may be presented simultaneously with a video of the patient in real-time or near real-time during a telemedicine or telehealth session on a user interface of a computing device of a medical professional. The video may also be accompanied by audio, text and other multimedia information and/or other sensorial or perceptive (e.g., tactile, gustatory, haptic, pressure-sensing-based or electromagnetic (e.g., neurostimulation), and without limitation, gesture recognition, gesture control, touchless user interfaces (TUIs), kinetic user interfaces (KUIs), tangible user interfaces, wired gloves, depth-aware cameras, stereo cameras, and gesture-based controllers. Real-time may refer to less than or equal to 2 seconds. Near real-time may refer to any interaction of a sufficiently short time to enable two individuals to engage in a dialogue via such user interface, and will generally be less than 10 seconds (or any suitably proximate difference between two different times) but greater than 2 seconds.

FIGS. 1-11, discussed below, and the various embodiments used to describe the principles of this disclosure are by way of illustration only and should not be construed in any way to limit the scope of the disclosure.

Figure 2:
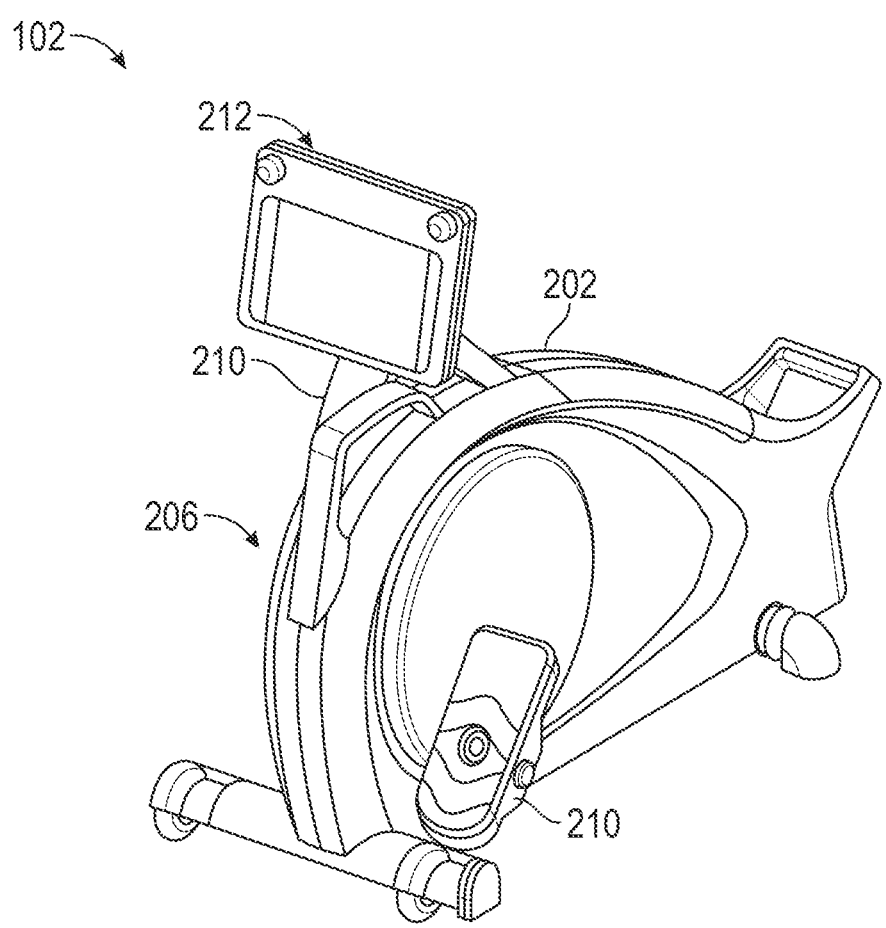
FIG. 2 generally illustrates an example medical device according to the principles of the present disclosure.

FIG. 1 illustrates a component diagram of an illustrative medical system 100 in accordance with aspects of this disclosure. The medical system 100 may include a medical device 102. The medical device 102 may be a testing device, a diagnostic device, a therapeutic device, or any other suitable medical device. "Medical device" as used in this context means any hardware, software, mechanical or other device, such as a treatment device (e.g., medical device 102, treatment device 10, or the like), that may assist in a medical service, regardless of whether it is FDA (or other governmental regulatory body of any given country) approved, required to be FDA (or other governmental regulatory body of any given country) approved or available commercially or to consumers without such approval. Non-limiting examples of medical devices include a thermometer, an MRI machine, a CT-scan machine, a glucose meter, an apheresis machine, and a physical therapy machine such as a physical therapy cycle. Non-limiting examples of places where the medical device 102 may be located include a healthcare clinic, a physical rehabilitation center, and a user's home to allow for telemedicine treatment, rehabilitation, and/or testing. FIG. 2 illustrates an example of the medical device 102 where the medical device 102 is a physical therapy cycle.

As generally illustrated in FIG. 2, the medical device 102 may comprise an electromechanical device, such as a physical therapy device. FIG. 2 generally illustrates a perspective view of an example of a medical device 102 according to certain aspects of this disclosure. Specifically, the medical device 102 illustrated is an electromechanical device 202, such as an exercise and rehabilitation device (e.g., a physical therapy device or the like). The electromechanical device 202 is shown having pedal 210 on opposite sides that are adjustably positionable relative to one another on respective radially-adjustable couplings 208. The depicted electromechanical device 202 is configured as a small and portable unit so that it is easily transported to different locations at which rehabilitation or treatment is to be provided, such as at patients' homes, alternative care facilities, or the like. The patient may sit in a chair proximate the electromechanical device 202 to engage the electromechanical device 202 with the patient's feet, for example. The electromechanical device 202 includes a rotary device such as radially-adjustable couplings 208 or flywheel or the like rotatably mounted such as by a central hub to a frame or other support. The pedals 210 are configured for interacting with a patient to be rehabilitated and may be configured for use with lower body extremities such as the feet, legs, or upper body extremities, such as the hands, arms, and the like. For example, the pedal 210 may be a bicycle pedal of the type having a foot support rotatably mounted onto an axle with bearings. The axle may or may not have exposed end threads for engaging a mount on the radially-adjustable coupling 208 to locate the pedal on the radially-adjustable coupling 208. The radially-adjustable coupling 208 may include an actuator configured to radially adjust the location of the pedal to various positions on the radially-adjustable coupling 208.

Alternatively, the radially-adjustable coupling 208 may be configured to have both pedals 210 on opposite sides of a single coupling 208. In some embodiments, as depicted, a pair of radially-adjustable couplings 208 may be spaced apart from one another but interconnected to an electric motor 206. In the depicted example, the computing device 104 may be mounted on the frame of the electromechanical device 202 and may be detachable and held by the user while the user operates the electromechanical device 202. The computing device 104 may present the patient portal 212 and control the operation of the electric motor 206, as described herein.

In some embodiments, as described in U.S. Pat. No. 10,173,094 (U.S. application Ser. No. 15/700,293), which is incorporated by reference herein in its entirety for all purposes, the medical device 102 may take the form of a traditional exercise/rehabilitation device which is more or less non-portable and remains in a fixed location, such as a rehabilitation clinic or medical practice. The medical device 102 may include a seat and is less portable than the medical device 102 shown in FIG. 2. FIG. 2 is not intended to be limiting: the electromechanical device 202 may include more or fewer components than those illustrated in FIG. 2.

Figure 9:
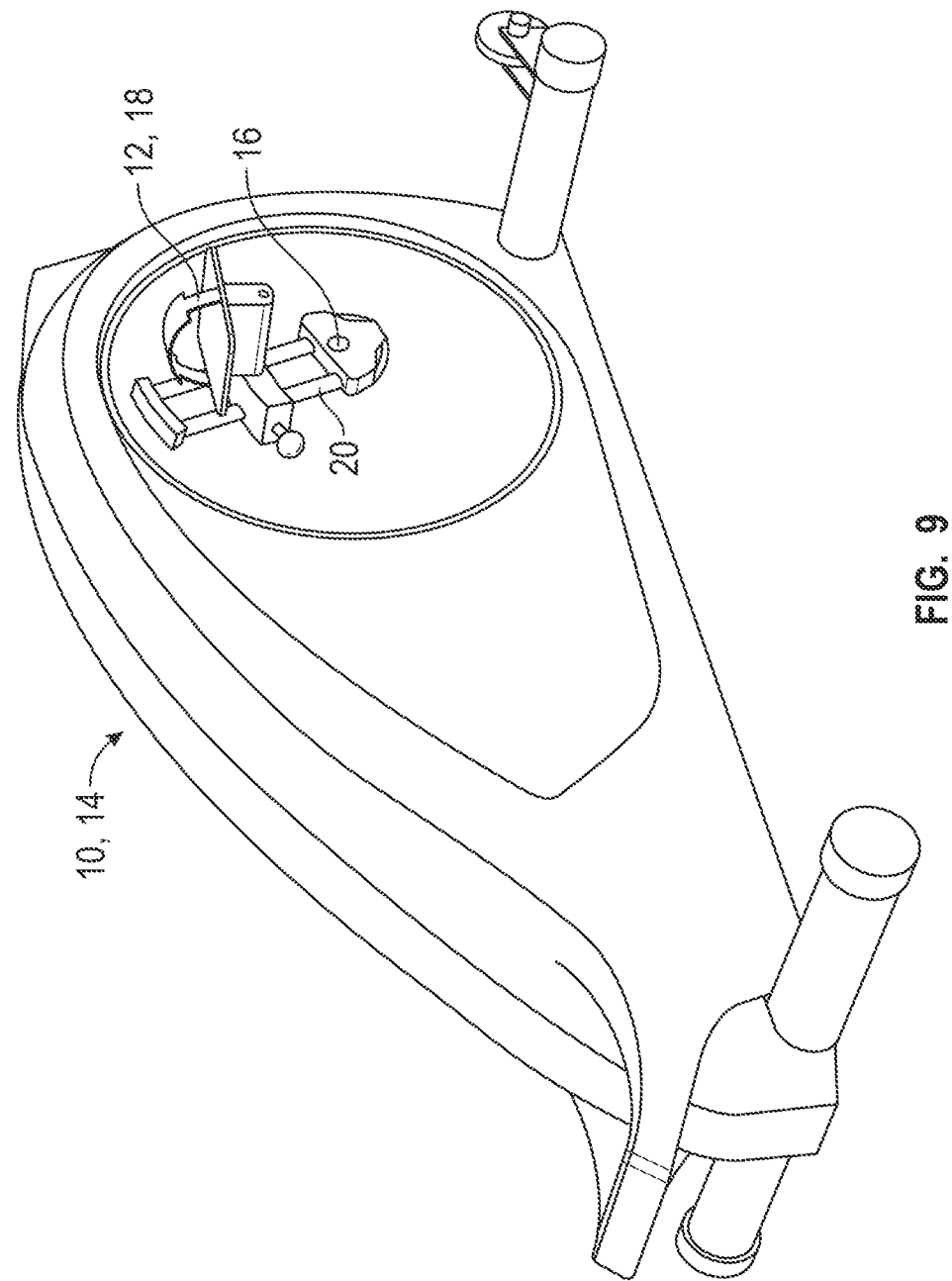
FIG. 9 generally illustrates a perspective view of an embodiment of the device, such as a treatment device, according to certain aspects of this disclosure.
Figure 10:
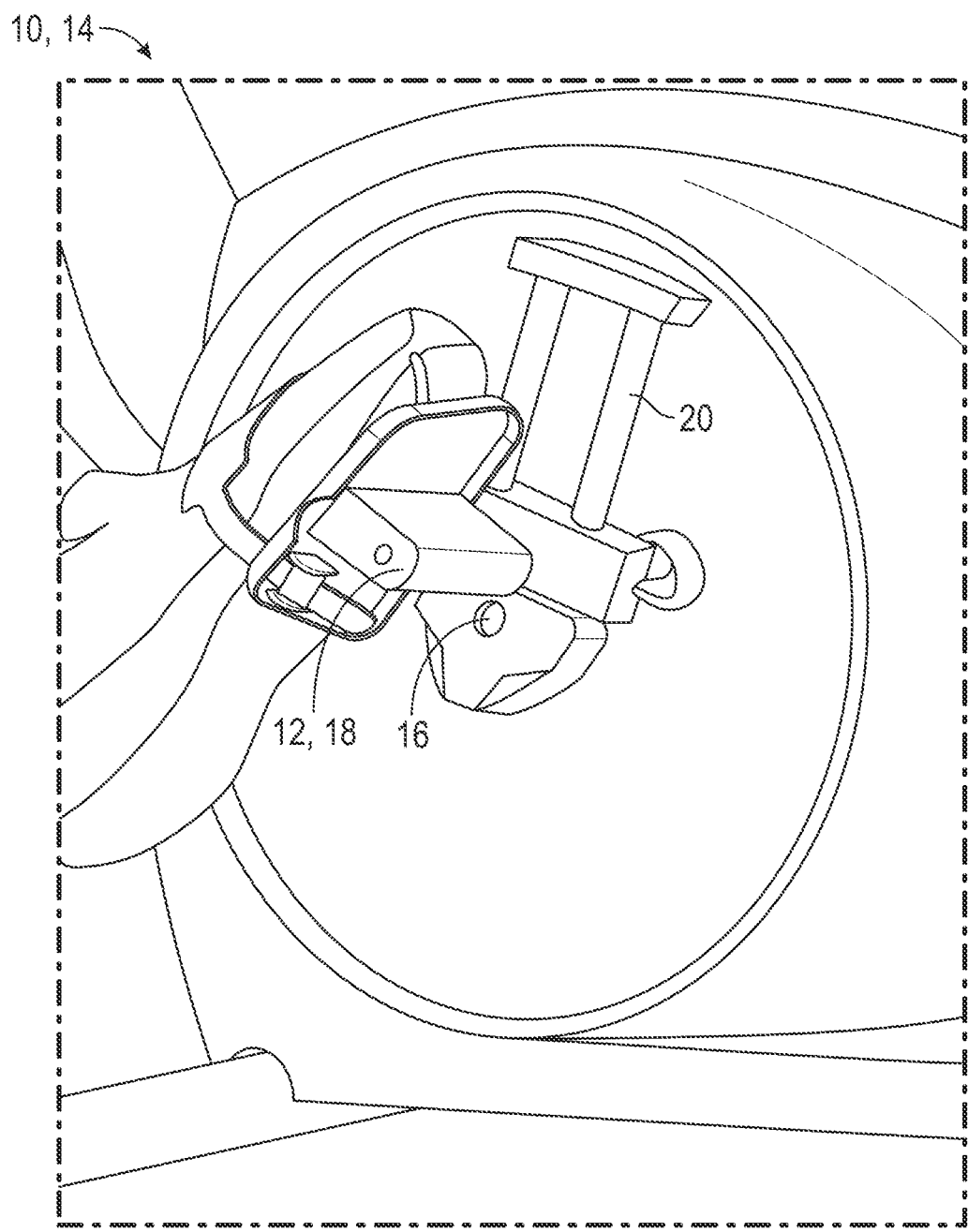
FIG. 10 generally illustrates a perspective view of a pedal of the treatment device of FIG. 9 according to certain aspects of this disclosure.

FIGS. 9-10 generally illustrate an embodiment of a treatment device, such as a treatment device 10. More specifically, FIG. 9 generally illustrates a treatment device 10 in the form of an electromechanical device, such as a stationary cycling machine 14, which may be called a stationary bike, for short. The stationary cycling machine 14 includes a set of pedals 12 each attached to a pedal arm 20 for rotation about an axle 16. In some embodiments, and as generally illustrated in FIG. 10, the pedals 12 are movable on the pedal arm 20 in order to adjust a range of motion used by the patient in pedaling. For example, the pedals being located inwardly toward the axle 16 corresponds to a smaller range of motion than when the pedals are located outwardly away from the axle 16. A pressure sensor 18 is attached to or embedded within one of the pedals 12 for measuring an amount of force applied by the patient on the pedal 102. The pressure sensor 18 may communicate wirelessly to the treatment device 10 and/or to the patient interface 26. FIGS. 9-10 are not intended to be limiting: the treatment device 10 may include more or fewer components than those illustrated in FIGS. 9-10.

Figure 11:
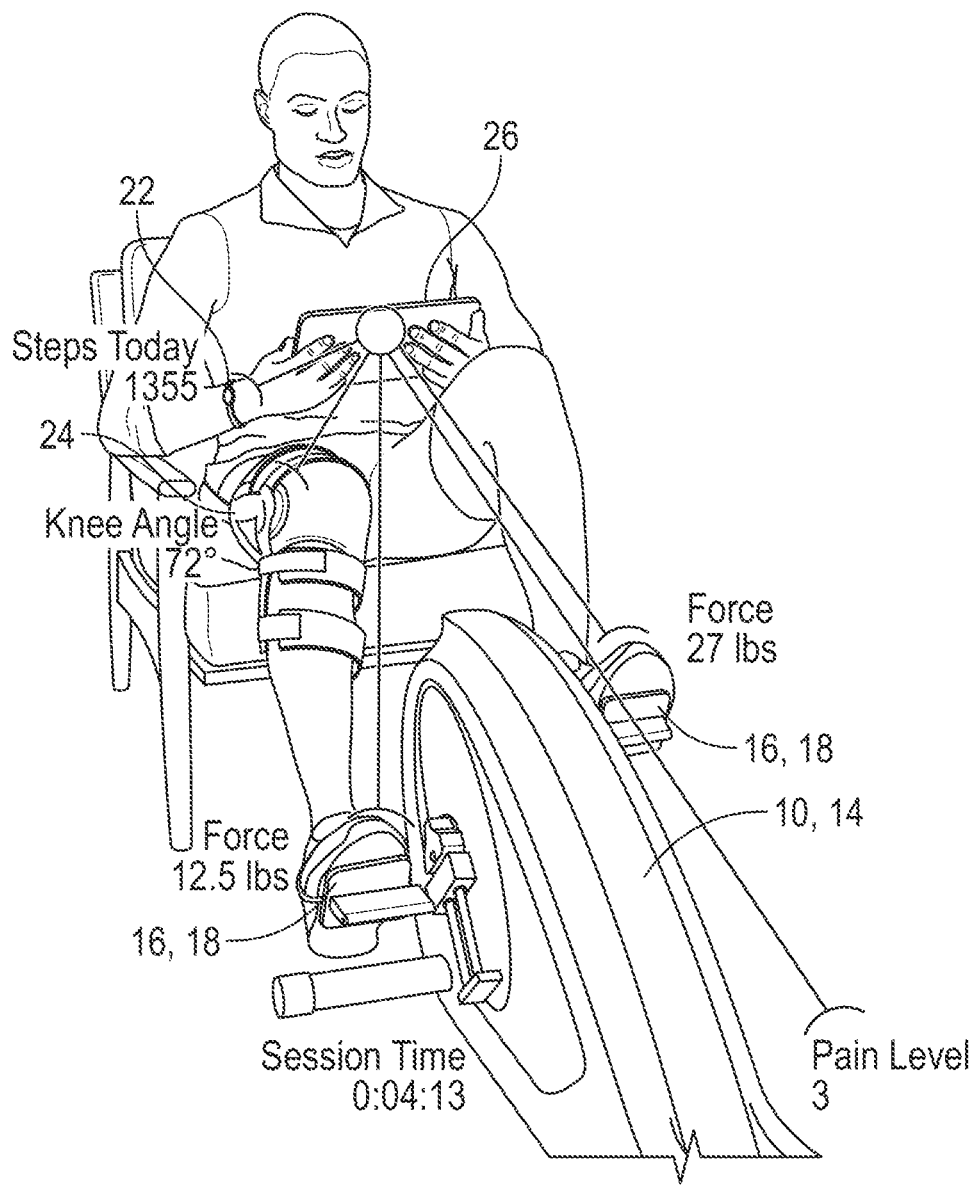
FIG. 11 generally illustrates a perspective view of a person using the treatment device of FIG. 9 according to certain aspects of this disclosure.

FIG. 11 generally illustrates a person (a patient) using the treatment device 10 of FIG. 9, and showing sensors and various data parameters connected to a patient interface 26. The example patient interface 26 is a tablet computer or smartphone, or a phablet, such as an iPad, an iPhone, an Android device, or a Surface tablet, which is held manually by the patient. In some other embodiments, the patient interface 26 may be embedded within or attached to the treatment device 10. FIG. 11 generally illustrates the patient wearing the ambulation sensor 22 on his wrist, with a note showing "STEPS TODAY 1355", indicating that the ambulation sensor 22 has recorded and transmitted that step count to the patient interface 26. FIG. 11 also generally illustrates the patient wearing the goniometer 24 on his right knee, with a note showing "KNEE ANGLE 72°", indicating that the goniometer 24 is measuring and transmitting that knee angle to the patient interface 26. FIG. 11 generally illustrates a right side of one of the pedals 12 with a pressure sensor 18 showing "FORCE 12.5 lbs.", indicating that the right pedal pressure sensor 18 is measuring and transmitting that force measurement to the patient interface 26. FIG. 11 also generally illustrates a left side of one of the pedals 12 with a pressure sensor 18 showing "FORCE 27 lbs.", indicating that the left pedal pressure sensor 18 is measuring and transmitting that force measurement to the patient interface 26. FIG. 11 also generally illustrates other patient data, such as an indicator of "SESSION TIME 0:04:13", indicating that the patient has been using the treatment device 10 for 4 minutes and 13 seconds. This session time may be determined by the patient interface 26 based on information received from the treatment device 10. FIG. 11 also generally illustrates an indicator showing "PAIN LEVEL 3". Such a pain level may be obtained from the patient in response to a solicitation, such as a question, presented upon the patient interface 26.

The medical device 102 may include, be coupled to, or be in communication with a computing device 104. The computing device 104 may include a processor 106. The processor 106 can include, for example, computers, intellectual property (IP) cores, application-specific integrated circuits (ASICs), programmable logic arrays, optical processors, programmable logic controllers, microcode, microcontrollers, servers, microprocessors, digital signal processors, any other suitable circuit, or any combination thereof.

The computing device 104 may include a memory device 108 in communication with the processor 106. The memory device 108 can include any type of memory capable of being accessed by a computer, such as read only memory (ROM), random access memory (RAM), a hard disk drive, a flash drive, a compact disc (CD), a digital video disc (DVD), a solid state drive (SSD), or any other suitable type of memory.

The computing device 104 may include an input device 110 in communication with the processor 106. Examples of the input device 110 include a keyboard, a keypad, a mouse, a microphone supported by speech-to-text software, or any other suitable input device. The input device 110 may be used by a medical system operator to input information, such as user identifying information, observational notes, or any other suitable information. An operator is to be understood throughout this disclosure to include both people and computer software, such as programs or artificial intelligence.

The computing device 104 may include an output device 112 in communication with the processor 106. The output device 112 may be used to provide information to the medical device operator or a user of the medical device 102. Examples of the output device 112 include a display screen, a speaker, an alarm system, or any other suitable output device, including haptic, tactile, olfactory, or gustatory ones, and without limitation, gesture recognition, gesture control, touchless user interfaces (TUIs), kinetic user interfaces (KUIs), tangible user interfaces, wired gloves, depth-aware cameras, stereo cameras, and gesture-based controllers. In some embodiments, such as where the computing device 104 includes a touchscreen, the input device 110 and the output device 112 may be the same device.

For communicating with remote computers and servers, the computing device 104 may include a network adapter 114 in communication with the processor 106. The network adapter 114 may include wired or wireless network adapter devices or a wired network port.

Any time information is transmitted or communicated, the information may be in EDI file format or any other suitable file format. In any of the methods or steps of the method, file format conversions may take place. By utilizing Internet of Things (IoT) gateways, data streams, ETL bucketing, EDI mastering, or any other suitable technique, data can be mapped, converted, or transformed into a carrier preferred state. As a result of the volume of data being transmitted, the data security requirements, and the data consistency requirements, enterprise grade architecture may be utilized for reliable data transfer.

FIG. 1 is not intended to be limiting; the medical system 100 and the computing device 104 may include more or fewer components than those illustrated in FIG. 1.

Figure 3:
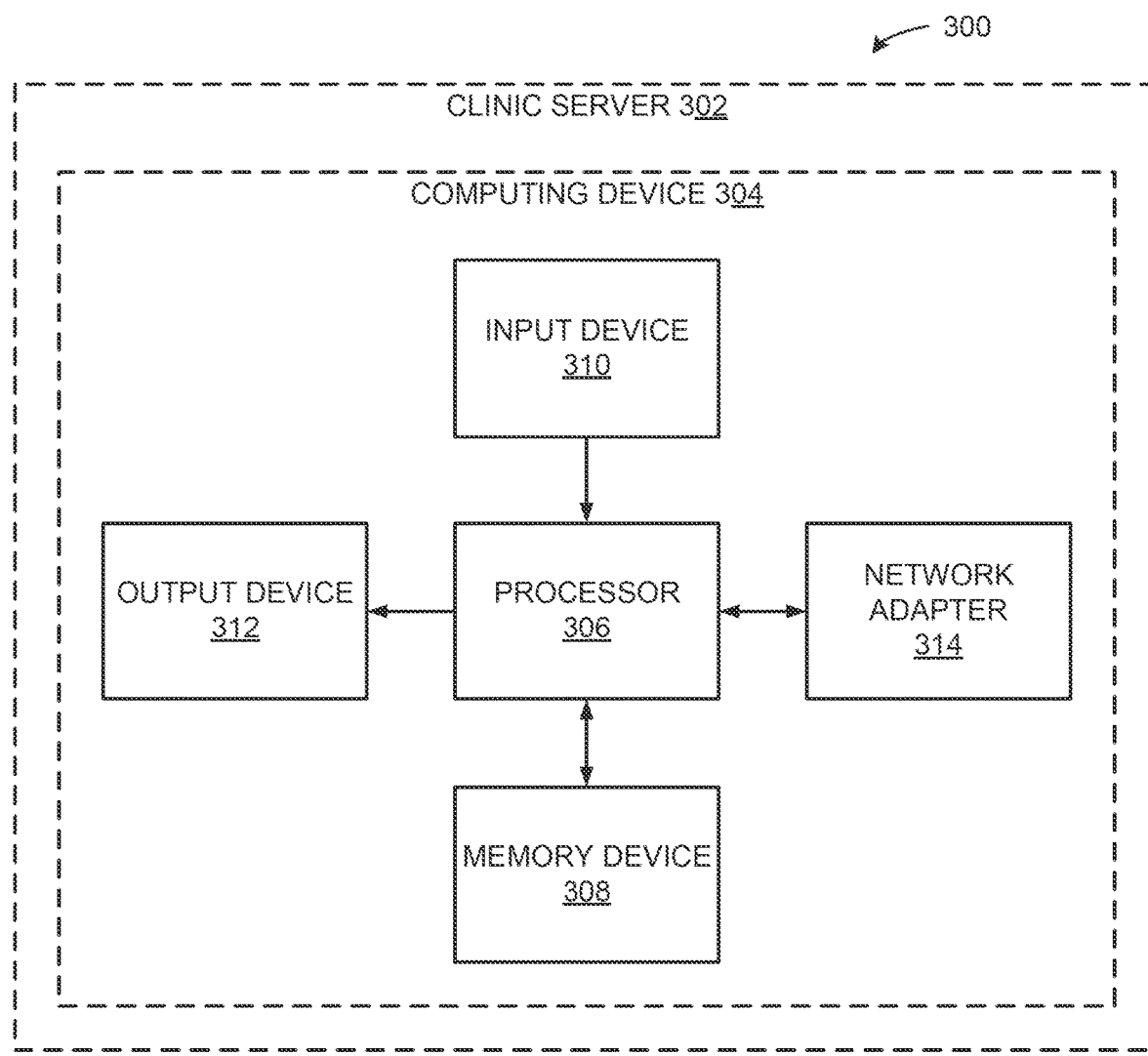
FIG. 3 generally illustrates a component diagram of an illustrative clinic server system according to the principles of the present disclosure.

FIG. 3 illustrates a component diagram of an illustrative clinic server system 300 in accordance with aspects of this disclosure. The clinic server system 300 may include a clinic server 302. The clinic server system 300 or clinic server 302 may be servers owned or controlled by a medical clinic (such as a doctor's office, testing site, or therapy clinic) or by a medical practice group (such as a testing company, outpatient procedure clinic, diagnostic company, or hospital). The clinic server 302 may be proximate to the medical system 100. In other embodiments, the clinic server 302 may be remote from the medical system 100. For example, during telemedicine-based or telemedicine-mediated treatment, rehabilitation, or testing, the clinic server 302 may be located at a healthcare clinic and the medical system 100 may be located at a patient's home. The clinic server 302 may be a rackmount server, a router computer, a personal computer, a portable digital assistant, a smartphone, a laptop computer, a tablet computer, a netbook, a desktop computer, any other suitable computing device, or any combination of the above. The clinic server 302 may be cloud-based or be a real-time software platform, and it may include privacy (e.g., anonymization, pseudonymization, or other) software or protocols, and/or include security software or protocols. The clinic server 302 may include a computing device 304. The computing device 304 may include a processor 306. The processor 306 can include, for example, computers, intellectual property (IP) cores, application-specific integrated circuits (ASICs), programmable logic arrays, optical processors, programmable logic controllers, microcode, microcontrollers, servers, microprocessors, digital signal processors, any other suitable circuit, or any combination thereof.

The computing device 304 may include a memory device 308 in communication with the processor 306. The memory device 308 can include any type of memory capable of being accessed by a computer, such as read only memory (ROM), random access memory (RAM), a hard disk drive, a flash drive, a compact disc (CD), a digital video disc (DVD), a solid state drive (SSD), or any other suitable type of memory.

The computing device 304 may include an input device 310 in communication with the processor 306. Examples of the input device 310 include a keyboard, a keypad, a mouse, a microphone supported by speech-to-text software, or any other suitable input device.

The computing device 304 may include an output device 312 in communication with the processor 106. Examples of the output device 312 include a display screen, a speaker, or any other suitable output device, including haptic, tactile, olfactory, or gustatory ones, and without limitation, gesture recognition, gesture control, touchless user interfaces (TUIs), kinetic user interfaces (KUIs), tangible user interfaces, wired gloves, depth-aware cameras, stereo cameras, and gesture-based controllers. In some embodiments, such as where the computing device 304 includes a touchscreen, the input device 310 and the output device 312 may be the same device.

The computing device 304 may include a network adapter 314 in communication with the processor 306 for communicating with remote computers and/or servers. The network adapter 314 may include wired or wireless network adapter devices.

FIG. 3 is not intended to be limiting; the clinic server system 300, the clinic server 302, and the computing device 304 may include more or fewer components than those illustrated in FIG. 3.

Figure 4:
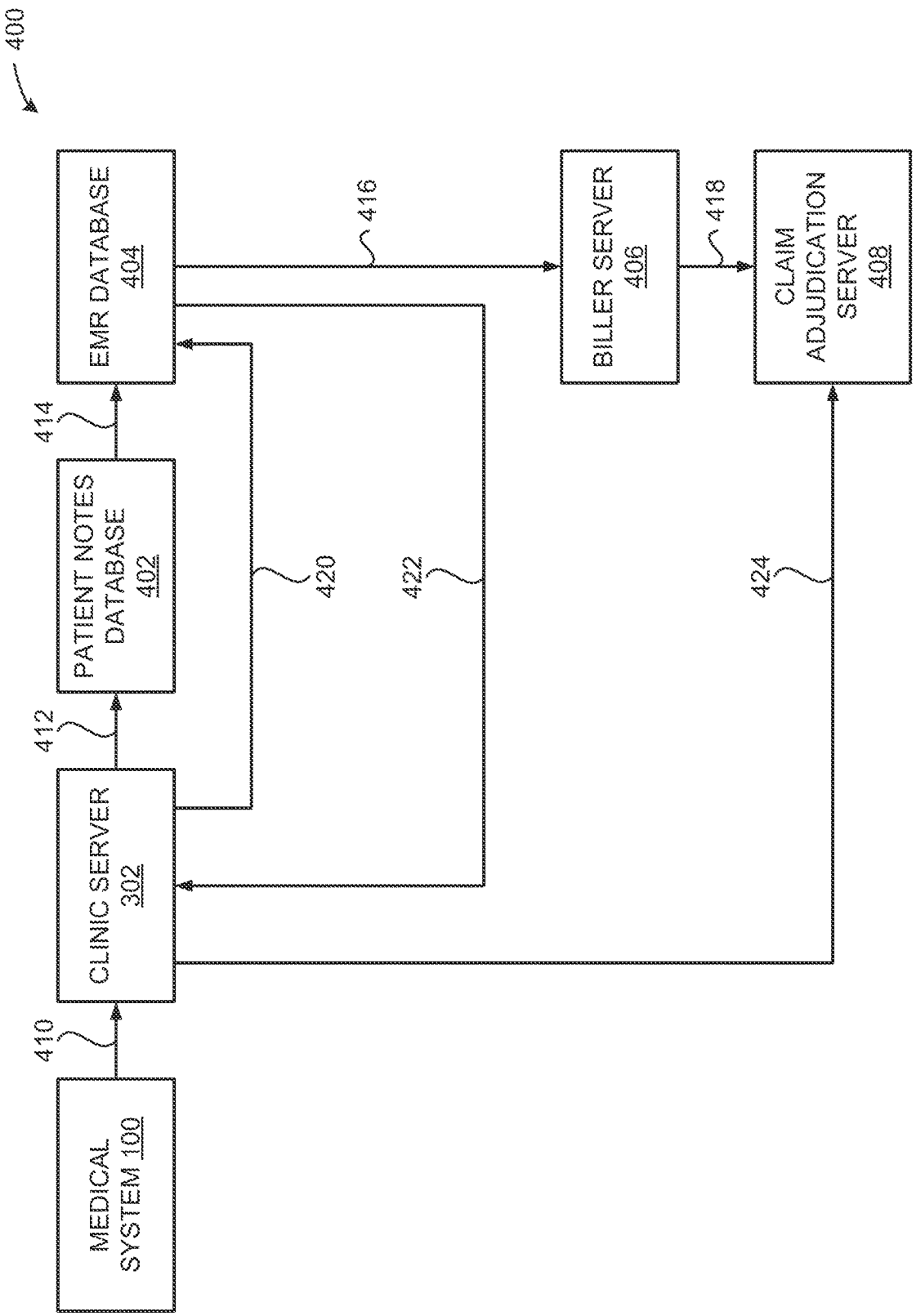
FIG. 4 generally illustrates a component diagram and method of an illustrative medical claim processing system and information flow according to the principles of the present disclosure.

FIG. 4 illustrates a component diagram and method of an illustrative medical claim processing system 400 and information flow according to aspects of this disclosure. The medical claim processing system 400 may include the medical system 100. The medical claim processing system 400 may include a clinic server 302.

The medical claim processing system 400 may include a patient notes database 402. The medical claim processing system 400 may include an electronic medical records (EMR) database 404. One or both of the patient notes database 402 and the EMR database 404 may be located on the clinic server 302, on one or more remote servers, or on any other suitable system or server.

The medical claim processing system 400 may include a biller server 406. The biller server 406 may be owned or controlled by a medical practice group (such as a testing company, outpatient procedure clinic, diagnostic company, or a hospital), a health insurance company, a governmental entity, or any other organization (including third-party organizations) associated with medical billing procedures. The biller server 406 may be a rackmount server, a router computer, a personal computer, a portable digital assistant, a smartphone, a laptop computer, a tablet computer, a netbook, a desktop computer, any other suitable computing device, or any combination of the above. The biller server 406 may be cloud-based or be a real-time software platform, and it may include privacy (e.g., anonymization, pseudonymization, or other) software or protocols, and/or include security software or protocols. The biller server 406 may contain a computing device including any combination of the components of the computing device 304 as illustrated in FIG. 3. The biller server 406 may be proximate to or remote from the clinic server 302.

The medical claim processing system 400 may include a claim adjudication server 408. The claim adjudication server 408 may be owned or controlled by a health insurance company, governmental entity, or any other organization (including third-party organizations) associated with medical billing procedures. The claim adjudication server 408 may be a rackmount server, a router computer, a personal computer, a portable digital assistant, a smartphone, a laptop computer, a tablet computer, a netbook, a desktop computer, any other suitable computing device, or any combination of the above. The claim adjudication server 408 may be cloud-based or be a real-time software platform, and it may include privacy (e.g., anonymization, pseudonymization, or other) software or protocols, and/or include security software or protocols. The claim adjudication server 408 may contain a computing device including any combination of the components of the computing device 304 as illustrated in FIG. 3. The claim adjudication server 408 may be proximate to or remote from the biller server 406. The claim adjudication server 408 may be configured to make or receive a determination about whether a claim should be paid.

At step 410, device-generated information may be transmitted from the medical system 100 to the clinic server 302. The device-generated information may include medical result information generated by the medical device 102. Medical result information can include information pertaining to a patient's medical condition and can include, without limitation, medical test results. Such medical test results can include, without limitation, CT scans, X-ray images, blood test results, and/or biopsy results. For example, the CT scans may include medical result information pertaining to a patient's medical condition.

The device-generated information may include medical coding information generated by the medical device 102. Medical coding information refers, without limitation, to medical information represented by a code, such as a DRG, an ICD-10 code, or other codes embodying, representing, or encoding information related to a medical procedure or a medical test. Medical coding information can be device-based. Such device-based medical coding information (e.g., an ICD-10 code) can be derived from device-generated information (e.g., a CT scan), produced by, or otherwise sourced from a medical device (e.g., CT machine) or actions performed by, with, or on a medical device (e.g., rehabilitation on a physical therapy cycle). Device-based medical coding information can be used to supplement and/or replace medical coding information from alternative sources (e.g., remote databases, billing agencies, etc.). In an example where telemedicine is used to facilitate or mediate blood glucose testing on a patient using a glucose meter located at the patient's home or carried by the patient, device-generated information may include medical coding information (e.g., an ICD-10 code) indicating that a procedure, such as a blood glucose test, was performed by using a glucose meter and that the glucose meter generated blood glucose test results. In this example, the glucose meter (a medical device) produces device-generated information when it produces the blood glucose test results and when it generates the medical coding information. The medical system 100 and the clinic server 302 may be communicatively coupled via the network adapter 114. The device-generated information may be transmitted from the medical system 100 to the clinic server 302 via, for example, the network adapter 114.

At step 412, clinic server information may be transmitted from clinic server 302 to the patient notes database 402. The clinic server information may include medical result information generated by the medical device 102. Using the device-generated information received from the medical device 10, the clinic server information may include device-based medical result information determined by the clinic server 302. The clinic server information may include medical coding information generated by the medical device 102. Using the device-generated information received from the medical device 102, the clinic server information may include device-based medical coding information determined by the clinic server 302, including a DRG, an ICD-10, or another code generated by the medical device 102 and determined to be valid by the clinic server 302. The clinic server information may include an ICD-10 code that is determined using an analysis of the device-generated information. An example of determining the ICD-10 code using the analysis of the device-generated information includes the following: 1) the clinic server 302 identifies the image from the MRI scan as being an MRI scan of an upper spine of a patient, and 2) the clinic server 302 determines the ICD-10 code associated with the MRI scan of the upper spine. A clinic operator may also enter additional information into the patient notes database 402. For example, a doctor may enter additional medical result information and additional medical coding information into the patient notes database 402.

At step 414, patient notes information may be transmitted from the patient notes database 402 to the EMR database 404. The patient notes information may include medical result information generated by the medical device 102. Using the device-generated information received from the medical device 102, the patient notes information may include device-based medical result information determined by the clinic server 302. The patient notes information may include reviewed medical coding information (i.e., medical coding information that has been reviewed and/or input by a clinic operator). The patient notes information may include additional medical coding or result information entered by the clinic operator. A clinic operator may make a decision about what patient notes information should be or is transmitted from the from the patient notes database 402 to the EMR database 404. For example, a clinic operator may determine that it is not necessary to transmit a portion of the medical result information generated by the medical device 102, as, e.g., that information could be test data that does not reflect factual medical results of tests performed on a patient.

At step 416, EMR information may be transmitted from the EMR database 404 to the biller server 406. The EMR information may include medical result information generated by the medical device 102. Using the device-generated information received from the medical device 102, the EMR information may include device-based medical result information determined by the clinic server 302. The EMR information may include reviewed medical coding information. The EMR information may include additional medical result information entered by the clinic operator. The EMR information may include additional medical coding information entered by the clinic operator. A clinic operator may make a decision about which EMR information is transmitted from the EMR database 404 to the biller server 406. For example, a clinic operator may determine that it is not necessary to transmit a portion of the medical result information generated by the medical device 102, as, e.g., that information may be test data that does not reflect factual medical results of tests performed on a patient. A biller operator may enter biller notes into the biller server 406.

At step 418, biller information may be transmitted from the biller server 406 to the claim adjudication server 408. The biller information may include medical result information generated by the medical device 102. Using the device-generated information received from the medical device 102, the biller information may include device-based medical result information determined by the clinic server 302. The biller information may include reviewed medical coding information. The biller information may include additional medical result information entered by the clinic operator. The biller information may include additional medical coding information entered by the clinic operator. The biller information may include biller notes entered by the biller operator. For example, a biller operator may enter biller notes to pay in full, pay a reduced amount, reject the bill, or add any other suitable note. A biller operator may make a decision about which biller information is transmitted from the biller server 406 to the claim adjudication server 408. For example, the biller operator may determine that certain biller information is suspect and requires additional review, flag that biller information for review, and not send that information to claim adjudication.

At step 420, clinic server information may be transmitted from the clinic server 302 to the EMR database 404. The clinic server information may include medical result information generated by the medical device 102. Using the device-generated information received from the medical device 102, the clinic server information may include device-based medical result information determined by the clinic server 302. The clinic server information may include medical coding information generated by the medical device 102. Using the device-generated information received from the medical device 102, the clinic server information may include device-based medical coding information determined by the clinic server 302. Bypassing the patient notes database 402 may allow for unmodified clinic server information to be entered into the electronic medical records.

At step 422, information may be transmitted from the EMR database 404 to the clinic server 302. The information may include additional medical result or coding information entered by the clinic operator. The information may include reviewed medical coding information approved or modified by the clinic operator. The clinic server 302 may cross-reference the medical coding information that was sent by the clinic server 302 and the information that was received by the clinic server 302. The clinic server 302 may determine whether the medical coding information received by the clinic server 302 can be reconciled with the medical coding information sent by the clinic server 302. In the context of this application, "reconciled" or "reconcilable" means that the medical coding information received by the clinic server 302 and the medical coding information sent by the clinic server 302 are not contradictory. For instance, if a knee injury is indicated, but an elbow surgery is performed, the two are not reconcilable. However, if an elbow injury is indicated, and an elbow surgery is performed, the two are reconcilable.

At step 424, information may be transmitted from the clinic server 302 to the claim adjudication server 408. The information may include medical result information generated by the medical device 102. Using the device-generated information received from the medical device 102, the information may include device-based medical result information determined by the clinic server 302. The information may include medical coding information generated by the medical device 102. Using the device-generated information received from the medical device 102, the information may include device-based medical coding information determined by the clinic server 302. The information may include additional medical result and coding information entered by the clinic operator. The information may include reviewed medical coding information. The information may include the determination about whether the medical coding information received by the clinic server 302 can be reconciled with the medical coding information sent by the clinic server 302. By transmitting the device-based medical coding information directly to the claim adjudication server 408, fewer total data packets may be transmitted, reducing total processor and network loads. This is as compared to current systems, where all medical coding information is transmitted a multitude of times: through, inter alia, patient notes databases 402, EMR databases 404, biller servers 406, and finally claim adjudication servers 408.

FIG. 4 is not intended to be limiting; medical claim processing system 400 and any sub-components thereof may include more or fewer components, steps, and/or processes than those illustrated in FIG. 4. Any or all of the methods described may be implemented during a telemedicine session or at any other desired time.

Figure 5:
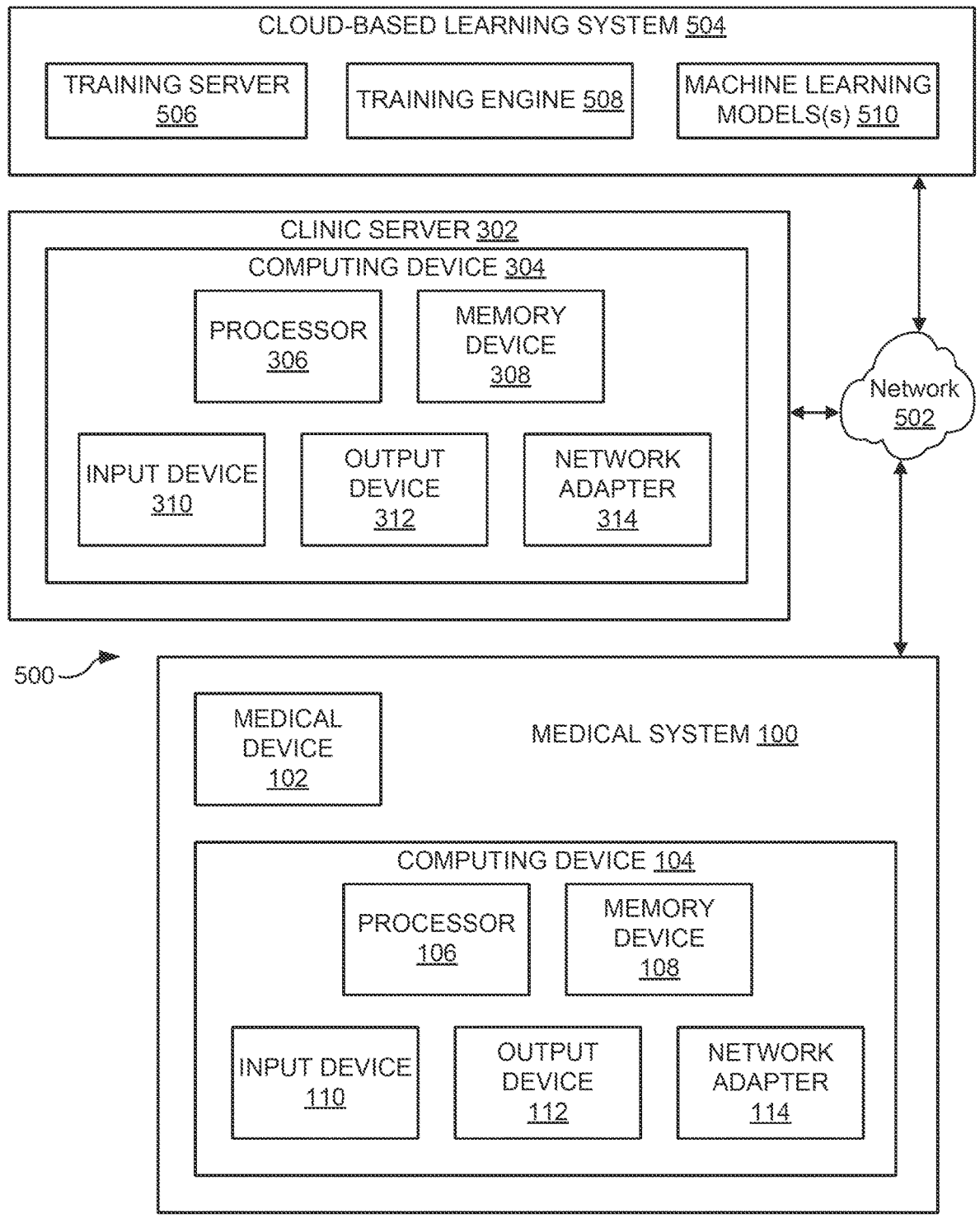
FIG. 5 generally illustrates a component diagram of an alternative arrangement of an illustrative medical claim processing system according to the principles of the present disclosure.

FIG. 5 illustrates a component diagram of an illustrative medical claim processing system 500 according to aspects of this disclosure. The medical claim processing system 500 can include the medical system 100 of FIG. 1. The medical system 100 may be in communication with a network 502. The network 502 may be a public network (e.g., connected to the Internet via wired (Ethernet) or wireless (Wi-Fi)), a private network (e.g., a local area network (LAN) or wide area network (WAN)), a combination thereof, or any other suitable network.

The medical claim processing system 500 can include the clinic server 302 of FIG. 3. The clinic server 302 may be in communication with the network 502.

The medical claim processing system 500 can include a cloud-based learning system 504. The cloud-based learning system 504 may be in communication with the network 502. The cloud-based learning system 504 may include one or more training servers 506 and form a distributed computing architecture. Each of the training servers 506 may include a computing device, including any combination of one or more of the components of the computing device 304 as illustrated in FIG. 3, or any other suitable components. The training servers 506 may be in communication with one another via any suitable communication protocol. The training servers 506 may store profiles for users including, but not limited to, patients, clinics, practice groups, and/or insurers. The profiles may include information such as historical device-generated information, historical device-based medical coding information, historical reviewed medical coding information, historical computer-based determinations on whether the reviewed medical coding information can be reconciled with the device-based coding information, and historical human-based determinations on whether the reviewed medical coding information has been reconciled with the device-based coding information. Other non-limiting examples of desired historical information can include any information relating to a specific patient, condition, or population that was recorded at a time prior to the interaction being billed as the medical claim.

In some aspects, the cloud-based learning system 504 may include a training engine 508 capable of generating one or more machine learning models 510. The machine learning models 510 may be trained to generate "determination" algorithms that, using the device-generated information, aid in determining device-based medical coding information. For instance, if the medical device 102 is an MRI, the machine learning models 510 may generate progressively more accurate algorithms to determine, using device-generated information such as MRI images, which type of MRI was performed and which type of medical coding information to associate with the type of MRI performed. To generate the one or more machine learning models 510, the training engine 508 may train the one or more machine learning models 510. The training engine 508 may use a base data set of historical device-generated information, historical device-based medical coding information, historical reviewed medical coding information, any other desired historical information and/or historical computer-based or human-based determinations on whether the reviewed medical coding information can be reconciled with the device-based coding information. The training engine 508 may be a rackmount server, a router computer, a personal computer, a portable digital assistant, a smartphone, a laptop computer, a tablet computer, a netbook, a desktop computer, an Internet of Things (IoT) node or sensor, any other suitable computing device, or any combination of the above. The training engine 508 may be cloud-based or be a real-time software platform, include privacy-enhancing, privacy-preserving or privacy modifying software or protocols, and/or include security software or protocols. Using training data that includes training inputs and corresponding target outputs, the one or more machine learning models 510 may refer to model artifacts created by the training engine 508. The training engine 508 may find patterns in the training data that map the training input to the target output and generate the machine learning models 510 that identify, store, or use these patterns. Although depicted separately from the medical system 100, the clinic server 302, the biller server 406, the claim adjudication server 408, the training engine 508, and the machine learning models 510 may reside on the medical system 100. Alternatively, the clinic server 302, the biller server 406, the claim adjudication server 408, the training engine 508, and the machine learning models 510 may reside on the clinic server 302, the biller server 406, the claim adjudication server 408, and/or any other suitable server.

The machine learning models 510 may include one or more neural networks, such as an image classifier, a recurrent neural network, a convolutional network, a generative adversarial network, a fully connected neural network, any other suitable network, or any combination thereof. In some embodiments, the machine learning models 510 may be composed of a single level of linear or non-linear operations or may include multiple levels of non-linear operations. For example, the machine learning models 510 may include numerous layers and/or hidden layers that perform calculations (e.g., dot products) using various neural nodes.

FIG. 5 is not intended to be limiting; the medical claim processing system 500, the medical system 100, the computing device 104, the clinic server 302, the clinic server 302, the computing device 304, the cloud-based learning system 504, and any sub-components thereof may include more or fewer components than those illustrated in FIG. 5. Any or all of the methods described may be implemented during a telemedicine session or at any other desired time.

Figure 6:
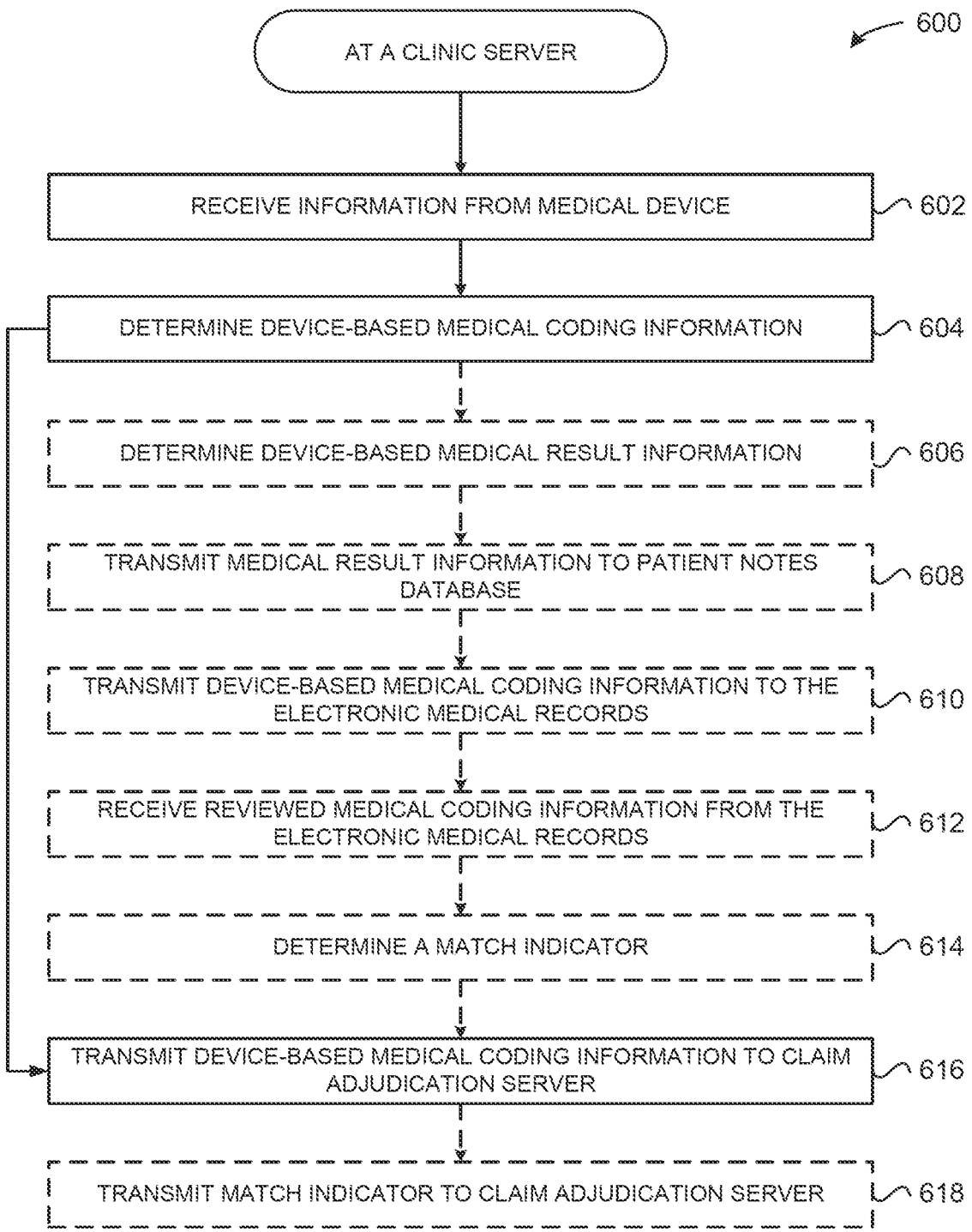
FIG. 6 generally illustrates a method of processing medical claims at a clinic server according to the principles of the present disclosure.

FIG. 6 illustrates a computer-implemented method 600 for a clinic server 302 processing medical claims. The method 600 may be implemented on a system including a processor, such as the processor 306, and a memory device, such as the memory device 308. The method 600 may be implemented on a processor configured to perform the steps of the method 600. The method 600 may be implemented on the clinic server system 300. The method 600 may include operations implemented in computer instructions stored in a memory device, such as the memory device 308, and executed by a processor, such as the processor 306, of a computing device, such as the computing device 304. The steps of the method 600 may be stored in a non-transient computer-readable storage medium.

At step 602, the method 600 can include receiving device-generated information from a medical device. The medical device may include the medical device 102 and/or the medical system 100. The device-generated information may include medical coding and/or medical result information.

At step 604, the method 600 can include, using the device-generated information, determining device-based medical coding information. This determination can include cross-referencing information about actions performed by the medical device 102 with a reference list associating those actions with certain medical codes. The reference list could be stored on the clinic server 302, the cloud-based learning system 504, or on any other suitable server, database, or system. Furthermore, this determination can include identifying a portion of the device-generated information containing medical coding information.

At step 606, the method 600 can include, using the information, determining device-based medical result information. This determination can include determining that the device-generated information includes test results (e.g., a blood glucose measurement, a cholesterol measurement, etc.), medical imaging data (e.g., an X-Ray image, an MRI image, etc.), or physical therapy (or rehabilitation) measurements (e.g., heart-rate, oxygen content, etc.).

At step 608, the method 600 can include transmitting the device-based medical result information to a patient notes database. The patient notes database can include the patient notes database 402.

At step 610, the method 600 can include transmitting the device-based medical coding information to the EMR database. The EMR database can include the EMR database 404.

At step 612, the method 600 can include receiving reviewed medical coding information from the EMR database. The EMR database can include the EMR database 404.

At step 614, the method 600 can include, using the reviewed medical coding information and the device-based medical coding information, determining a match indicator. The match indicator indicates whether the reviewed medical coding information can be reconciled with the device-based medical coding information. This determination can include cross-referencing the reviewed medical coding information with the device-based medical coding information to generate the match indicator. For example, both the reviewed medical coding information and the device-based medical coding information may be cross-referenced with a database to determine which reviewed medical coding information is and is not reconcilable with the device-based medical coding information. For instance, device-based medical coding information for a CT scan of a knee may be reconcilable with reviewed medical coding information of a patient being fitted for a knee brace, but not reconcilable with reviewed medical coding information of a patient being fitted for an elbow brace.

At step 616, the method 600 can include transmitting the device-based medical coding information directly to a claim adjudication server while bypassing the EMR database 404 and the biller server 406. The claim adjudication server may be the claim adjudication server 408. By transmitting the device-based medical coding information directly to the claim adjudication server 408, fewer total data packets may be sent, reducing network loads.

At step 618, the method 600 can include transmitting the determination of whether the reviewed medical coding information can be reconciled with the device-based medical coding information. The determination may be transmitted to the claim adjudication server 408. The determination may be transmitted to the biller server. The biller server may be the biller server 406. The determination may be transmitted to the patient notes database 402 or the EMR database 404 and/or to a personal computer or mobile device of a clinic operator.

FIG. 6 is not intended to be limiting; the method 600 can include more or fewer steps and/or processes than those illustrated in FIG. 6. Any or all of the steps of method 600 may be implemented during a telemedicine session or at any other desired time.

Figure 7:
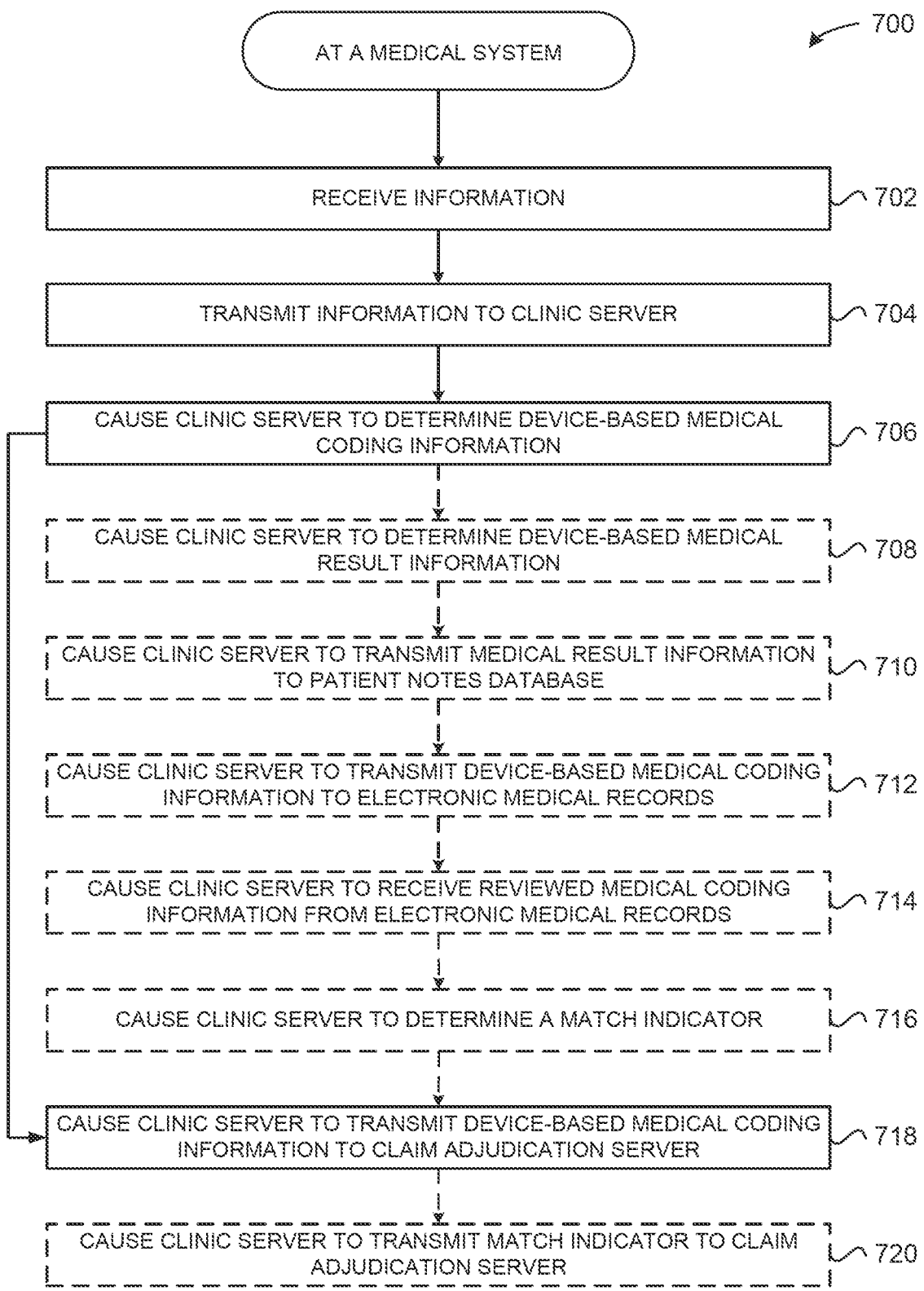
FIG. 7 generally illustrates a method of processing medical claims at a medical system according to the principles of the present disclosure.

FIG. 7 illustrates a computer-implemented method 700 for a medical system processing medical claims. The method 700 may be implemented on a system including a processor, such as the processor 106, and a memory device, such as the memory device 108. The method 700 may be implemented on a processor configured to perform the steps of the method 700. The method may be implemented on the medical system 100. The method 700 may include operations that are implemented in computer instructions stored in a memory device, such as the memory device 108, and executed by a processor, such as the processor 106, of a computing device, such as the computing device 104. The steps of the method 700 may be stored in a non-transient computer-readable storage medium.

At step 702, the method 700 can include transmitting the device-generated information to a clinic server. The clinic server may be the clinic server 302. The medical device may include the medical device 102. The medical device may include the medical system 100. The device-generated information may include medical coding or medical result information.

At step 704, the method 700 can include transmitting device-generated information to the clinic server 302.

At step 706, the method 700 can include causing the clinic server 302, using the device-generated information, to determine device-based medical coding information. This determination can include cross-referencing information about actions performed by the medical device 102 with a reference list associating those actions with certain medical codes and/or identifying a portion of the device-generated information containing medical coding information.

At step 708, the method 700 can include causing the clinic server 302 to determine device-based medical result information using the device-generated information. This determination can include determining that the device-generated information includes test results (such as a blood glucose measurement).

At step 710, the method 700 can include causing the clinic server 302 to transmit the medical result information to a patient notes database. The patient notes database can include the patient notes database 402.

At step 712, the method 700 can include causing the clinic server 302 to transmit the device-based medical coding information to the EMR database. The EMR database can include the EMR database 404.

At step 714, the method 700 can include causing the clinic server 302 to receive from the EMR database 404 reviewed medical coding information.

At step 716, using the reviewed medical coding information and the device-based medical coding information, the method 700 can include causing the clinic server 302 to determine a match indicator. The match indicator indicates whether the reviewed medical coding information can be reconciled with the device-based medical coding information. Examples of such determination include (i) cross-referencing the reviewed medical coding information with the device-based medical coding information and/or (ii) cross-referencing both the reviewed medical coding information and the device-based medical coding information with a database to generate the match indicator. For instance, the device-based medical coding information for a CT scan of a knee may be reconcilable with reviewed medical coding information of patient being fitted for a knee brace, but not reconcilable with reviewed medical coding information of a patient being fitted for an elbow brace.

At step 718, the method 700 can include causing the clinic server 302 to transmit the device-based medical coding information to a claim adjudication server while bypassing the EMR database 404 and the biller server 406. The claim adjudication server may be the claim adjudication server 408. By transmitting the device-based medical coding information directly to the claim adjudication server 408, fewer total data packets may be sent, reducing network loads.

At step 720, the method 700 can include causing the clinic server 302 to transmit the determination. The determination may be transmitted to the claim adjudication server. The claim adjudication server may be the claim adjudication server 408. The determination may be transmitted to the biller server. The biller server may be the biller server 406. The determination may be transmitted to the patient notes database 402 or the EMR database 404. The determination may be transmitted to a personal computer or mobile device of a clinic operator.

FIG. 7 is not intended to be limiting; the method 700 can include more or fewer steps and/or processes than those illustrated in FIG. 7. Any or all of the steps of method 700 may be implemented during a telemedicine session or at any other desired time.

Figure 8:
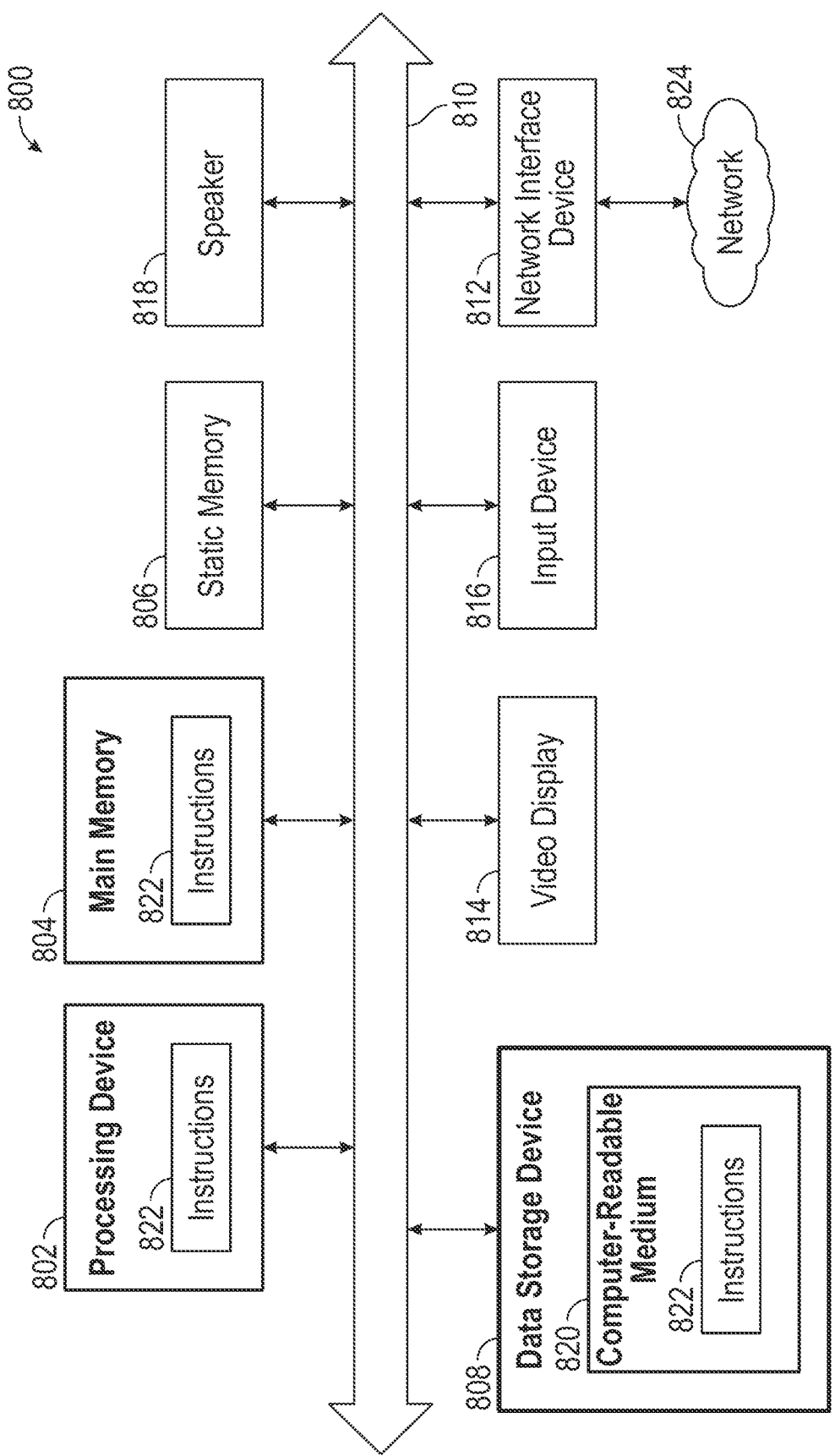
FIG. 8 generally illustrates an example computer system according to certain aspects of this disclosure.

FIG. 8 shows an example computer system 800 which can perform any one or more of the methods described herein, in accordance with one or more aspects of the present disclosure. In one example, computer system 800 may include a computing device and correspond to an assistance interface, a reporting interface, a supervisory interface, a clinician interface, a server (including an AI engine), a patient interface, an ambulatory sensor, a goniometer, a treatment device 10, a medical device 102, a pressure sensor, or any suitable component. The computer system 800 may be capable of executing instructions implementing the one or more machine learning models of the artificial intelligence engine. The computer system may be connected (e.g., networked) to other computer systems in a LAN, an intranet, an extranet, or the Internet, including via the cloud or a peer-to-peer network. The computer system may operate in the capacity of a server in a client-server network environment. The computer system may be a personal computer (PC), a tablet computer, a wearable (e.g., wristband), a set-top box (STB), a personal Digital Assistant (PDA), a mobile phone, a camera, a video camera, an Internet of Things (IoT) device, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 800 includes a processing device 802, a main memory 804 (e.g., read-only memory (ROM), flash memory, solid state drives (SSDs), dynamic random access memory (DRAM) such as synchronous DRAM (SDRAM)), a static memory 806 (e.g., flash memory, solid state drives (SSDs), static random access memory (SRAM)), and a data storage device 808, which communicate with each other via a bus 810.

Processing device 802 represents one or more general-purpose processing devices such as a microprocessor, central processing unit, or the like. More particularly, the processing device 802 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 802 may also be one or more special-purpose processing devices such as an application specific integrated circuit (ASIC), a system on a chip, a field programmable gate array (FPGA), a digital signal processor (DSP), network processor, or the like. The processing device 802 is configured to execute instructions for performing any of the operations and steps discussed herein.

The computer system 800 may further include a network interface device 812. The computer system 800 also may include a video display 814 (e.g., a liquid crystal display (LCD), a light-emitting diode (LED), an organic light-emitting diode (OLED), a quantum LED, a cathode ray tube (CRT), a shadow mask CRT, an aperture grille CRT, a monochrome CRT), one or more input devices 816 (e.g., a keyboard and/or a mouse or a gaming-like control), and one or more speakers 818 (e.g., a speaker). In one illustrative example, the video display 814 and the input device(s) 816 may be combined into a single component or device (e.g., an LCD touch screen).

The data storage device 816 may include a computer-readable medium 820 on which the instructions 822 embodying any one or more of the methods, operations, or functions described herein is stored. The instructions 822 may also reside, completely or at least partially, within the main memory 804 and/or within the processing device 802 during execution thereof by the computer system 800. As such, the main memory 804 and the processing device 802 also constitute computer-readable media. The instructions 822 may further be transmitted or received over a network via the network interface device 812.

While the computer-readable storage medium 820 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

FIG. 8 is not intended to be limiting; the system 800 may include more or fewer components than those illustrated in FIG. 8.

The term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium capable of storing, encoding or carrying a set of instructions for execution by the machine and causing the machine to perform any one or more of the methodologies of the present disclosure. The term "computer-readable storage medium" shall accordingly be taken to include, but not be limited to, solid-state memories, optical media, and magnetic media.

Any of the systems and methods described in this disclosure may be used in connection with rehabilitation. Unless expressly stated otherwise, is to be understood that rehabilitation includes prehabilitation (also referred to as "prehabilitation" or "prehab"). Prehabilitation may be used as a preventative procedure or as a pre-surgical or pre-treatment procedure. Prehabilitation may include any action performed by or on a patient (or directed to be performed by or on a patient, including, without limitation, remotely or distally through telemedicine) to, without limitation, prevent or reduce a likelihood of injury (e.g., prior to the occurrence of the injury); improve recovery time subsequent to surgery; improve strength subsequent to surgery; or any of the foregoing with respect to any non-surgical clinical treatment plan to be undertaken for the purpose of ameliorating or mitigating injury, dysfunction, or other negative consequence of surgical or non-surgical treatment on any external or internal part of a patient's body. For example, a mastectomy may require prehabilitation to strengthen muscles or muscle groups affected directly or indirectly by the mastectomy. As a further non-limiting example, the removal of an intestinal tumor, the repair of a hernia, open-heart surgery or other procedures performed on internal organs or structures, whether to repair those organs or structures, to excise them or parts of them, to treat them, etc., can require cutting through and harming numerous muscles and muscle groups in or about, without limitation, the abdomen, the ribs and/or the thoracic cavity. Prehabilitation can improve a patient's speed of recovery, measure of quality of life, level of pain, etc. in all the foregoing procedures. In one embodiment of prehabilitation, a pre-surgical procedure or a pre-non-surgical-treatment may include one or more sets of exercises for a patient to perform prior to such procedure or treatment. The patient may prepare an area of his or her body for the surgical procedure by performing the one or more sets of exercises, thereby strengthening muscle groups, improving existing and/or establishing new muscle memory, enhancing mobility, improving blood flow, and/or the like.

In some embodiments, the systems and methods described herein may use artificial intelligence and/or machine learning to generate a prehabilitation treatment plan for a user. Additionally, or alternatively, the systems and methods described herein may use artificial intelligence and/or machine learning to recommend an optimal exercise machine configuration for a user. For example, a data model may be trained on historical data such that the data model may be provided with input data relating to the user and may generate output data indicative of a recommended exercise machine configuration for a specific user. Additionally, or alternatively, the systems and methods described herein may use machine learning and/or artificial intelligence to generate other types of recommendations relating to prehabilitation, such as recommended reading material to educate the patient, a recommended health professional specialist to contact, and/or the like.

Consistent with the above disclosure, the examples of systems and method enumerated in the following clauses are specifically contemplated and are intended as a non-limiting set of examples.

Clause 1. A computer-implemented system for processing medical claims, comprising:
a medical device configured to be manipulated by a user while the user performs a treatment plan;
a patient interface associated with the medical device, the patient interface comprising an output configured to present telemedicine information associated with a telemedicine session; and
a processor configured to:
during the telemedicine session, receive device-generated information from the medical device;
using the device-generated information, determine device-based medical coding information; and
transmit the device-based medical coding information to a claim adjudication server.

Clause 2. The computer-implemented system of any clause herein, wherein, during the telemedicine session, the device-generated information is generated by the medical device.

Clause 3. The computer-implemented system of any clause herein, wherein, using the device-generated information, the processor is further configured to determine device-based medical result information.

Clause 4. The computer-implemented system of any clause herein, wherein the processor is further configured to transmit the device-based medical result information to a patient notes database.

Clause 5. The computer-implemented system of any clause herein, wherein the processor is further configured to transmit the device-based medical coding information to an electronic medical records database.

Clause 6. The computer-implemented system of any clause herein, wherein the processor is further configured to:
  receive reviewed medical coding information from an electronic medical records database, wherein, using the reviewed medical coding information and the device-based medical coding information, the processor is further configured to determine a match indicator; and
  transmit the match indicator to the claim adjudication server.

Clause 7. A system for processing medical claims, comprising:
  a processor configured to:
    receive device-generated information from a medical device;
    using the device-generated information, determine device-based medical coding information; and
    transmit the device-based medical coding information to a claim adjudication server.

Clause 8. The system of any clause herein, wherein the device-generated information is generated by the medical device.

Clause 9. The system of any clause herein, wherein, using the device-generated information, the processor is further configured to determine device-based medical result information.

Clause 10. The system of any clause herein, wherein the processor is further configured to transmit the device-based medical result information to a patient notes database.

Clause 11. The system of any clause herein, wherein the processor is further configured to transmit the device-based medical coding information to an electronic medical records database.

Clause 12. The system of any clause herein, wherein the processor is further configured to receive reviewed medical coding information from an electronic medical records database.

Clause 13. The system of any clause herein, wherein, using the reviewed medical coding information and the device-based medical coding information, the processor is further configured to determine a match indicator.

Clause 14. The system of any clause herein, wherein the processor is further configured to transmit the match indicator to the claim adjudication server.

Clause 15. The system of any clause herein, further comprising a memory device operatively coupled to the processor, wherein the memory device stores instructions, and wherein the processor is configured to execute the instructions.

Clause 16. A method for a clinic server processing medical claims, comprising:
  receiving device-generated information from a medical device;
  using the device-generated information, determining device-based medical coding information; and
  transmitting the device-based medical coding information to a claim adjudication server.

Clause 17. The method of any clause herein, wherein the device-generated information is generated by the medical device.

Clause 18. The method of any clause herein, further comprising using the device-generated information to determine device-based medical result information.

Clause 19. The method of any clause herein, further comprising transmitting the device-based medical result information to a patient notes database.

Clause 20. The method of any clause herein, further comprising transmitting the device-based medical coding information to an electronic medical records database.

Clause 21. The method of any clause herein, further comprising receiving reviewed medical coding information from an electronic medical records database.

Clause 22. The method of any clause herein, further comprising determining, using the reviewed medical coding information and the device-based medical coding information, a match indicator.

Clause 23. The method of any clause herein, further comprising transmitting the match indicator to the claim adjudication server.

Clause 24. A tangible, non-transitory computer-readable medium storing instructions that, when executed, cause a processor to:
  receive device-generated information from a medical device;
  using the device-generated information, determine device-based medical coding information; and
  transmit the device-based medical coding information to a claim adjudication server.

Clause 25. The tangible, non-transitory computer-readable medium of any clause herein, wherein the device-generated information is generated by the medical device.

Clause 26. The tangible, non-transitory computer-readable medium of any clause herein, wherein, using the device-generated information, the instructions further cause the processor to determine device-based medical result information.

Clause 27. The tangible, non-transitory computer-readable medium of any clause herein, wherein the instructions further cause the processor to transmit the device-based medical result information to a patient notes database.

Clause 28. The tangible, non-transitory computer-readable medium of any clause herein, wherein the instructions further cause the processor to transmit the device-based medical coding information to an electronic medical records database.

Clause 29. The tangible, non-transitory computer-readable medium of any clause herein, wherein the processor is further configured to receive reviewed medical coding information from an electronic medical records database.

Clause 30. The tangible, non-transitory computer-readable medium of any clause herein, wherein, using the reviewed medical coding information and the device-based medical coding information, the instructions further cause the processor to determine a match indicator.

Clause 31. The tangible, non-transitory computer-readable medium of any clause herein, wherein the instructions further cause the processor to transmit the match indicator to the claim adjudication server.

Clause 32. A system for generating and processing medical billing codes, comprising:
  a medical device; and
  a computing device comprising a processor in communication with the medical device, wherein the processor is configured to:
    receive device-generated information from the medical device;
    transmit the device-generated information to a clinic server;

using the device-generated information, cause the clinic server to determine device-based medical coding information; and cause the clinic server to transmit the device-based medical coding information to a claim adjudication server.

Clause 33. The system of any clause herein, wherein the device-generated information is generated by the medical device.

Clause 34. The system of any clause herein, wherein, using the device-generated information, the processor is further configured to cause the clinic server to determine device-based medical result information.

Clause 35. The system of any clause herein, wherein the processor is further configured to cause the clinic server to transmit the device-based medical result information to a patient notes database.

Clause 36. The system of any clause herein, wherein the processor is further configured to cause the clinic server to transmit the device-based medical coding information to an electronic medical records database.

Clause 37. The system of any clause herein, wherein the processor is further configured to cause the clinic server to receive reviewed medical coding information from an electronic medical records database.

Clause 38. The system of any clause herein, wherein the processor is further configured to cause the clinic server to, using the reviewed medical coding information and the device-based medical coding information, determine a match indicator.

Clause 39. The system of any clause herein, wherein the processor is further configured to cause the clinic server to transmit the match indicator to the claim adjudication server.

Clause 40. The system of any clause herein, wherein the computing device is operatively coupled to the medical device.

Clause 41. The system of any clause herein, wherein the computing device is integral to the medical device.

Clause 42. The system of any clause herein, further comprising a memory device operatively coupled to the processor, wherein the memory device stores instructions, and wherein the processor is configured to execute the instructions.

Clause 43. A method for operating a medical device, the method comprising:
receiving device-generated information from the medical device transmitting the device-generated information to a clinic server;
using the device-generated information, causing the clinic server to determine device-based medical coding information; and
causing the clinic server to transmit the device-based medical coding information to a claim adjudication server.

Clause 44. The method of any clause herein, wherein the device-generated information is generated by the medical device.

Clause 45. The method of any clause herein, further comprising using the device-generated information to cause the clinic server to determine device-based medical result information.

Clause 46. The method of any clause herein, further comprising causing the clinic server to transmit the device-based medical result information to a patient notes database.

Clause 47. The method of any clause herein, further comprising causing the clinic server to transmit the device-based medical coding information to an electronic medical records database.

Clause 48. The method of any clause herein, further comprising causing the clinic server to receive reviewed medical coding information from an electronic medical records database.

Clause 49. The method of any clause herein, further comprising causing the clinic server to determine a match indicator.

Clause 50. The method of any clause herein, further comprising causing the clinic server to transmit the match indicator to the claim adjudication server by using the reviewed medical coding information and the device-based medical coding information.

Clause 51. A tangible, non-transitory computer-readable medium storing instructions that, when executed, cause a processor to:
receive device-generated information from a medical device;
transmit the device-generated information to a clinic server;
using the device-generated information, cause the clinic server to determine device-based medical coding information; and
cause the clinic server to transmit the device-based medical coding information to a claim adjudication server.

Clause 52. The tangible, non-transitory computer-readable medium if any clause herein, wherein the device-generated information is generated by the medical device.

Clause 53. The tangible, non-transitory computer-readable medium of any clause herein, wherein the instructions further cause the processor to cause the clinic server to determine device-based medical result information.

Clause 54. The tangible, non-transitory computer-readable medium of any clause herein, wherein the instructions further cause the processor to cause the clinic server to transmit the device-based medical result information to a patient notes database.

Clause 55. The tangible, non-transitory computer-readable medium of any clause herein, wherein the instructions further cause the processor to cause the clinic server to transmit the device-based medical coding information to an electronic medical records database.

Clause 56. The tangible, non-transitory computer-readable medium of any clause herein, wherein the instructions further cause the processor to cause the clinic server to receive reviewed medical coding information from an electronic medical records database.

Clause 57. The tangible, non-transitory computer-readable medium of any clause herein, wherein, using the reviewed medical coding information and the device-based medical coding information, the instructions further cause the processor to cause the clinic server to determine a match indicator.

Clause 58. The tangible, non-transitory computer-readable medium of any clause herein, wherein the instructions further cause the processor to cause the clinic server to transmit the match indicator to the claim adjudication server.

No part of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle.

The foregoing description, for purposes of explanation, use specific nomenclature to provide a thorough understanding of the described embodiments. However, it should be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It should be apparent to one of ordinary skill in the art that many modifications and variations are possible in view of the above teachings.

The above discussion is meant to be illustrative of the principles and various embodiments of the present invention. Once the above disclosure is fully appreciated, numerous variations and modifications will become apparent to those skilled in the art. It is intended that the following claims be interpreted to embrace all such variations and modifications.

What is claimed is:

1. A computer-implemented system for processing medical claims, comprising:
    an electromechanical device configured to be manipulated by a user while the user performs a treatment plan;
    a patient interface associated with the electromechanical device and configured to present telemedicine information associated with a telemedicine session; and
    one or more processors configured to:
        generate one or more machine learning models trained to determine healthcare services provided during the telemedicine session based on device-generated information generated by the electromechanical device while the user performs the treatment plan;
        determine, by using the one or more machine learning models and based on the device-generated information, device-based coding information; and
        transmit the device-based coding information to a claim adjudication server,
    wherein the one or more processors are further configured to generate the one or more machine learning models using training data comprising: historical device-generated information; historical device-based coding information; historical reviewed coding information; historical computer-based determinations on whether the historical reviewed coding information can be reconciled with the historical device-based coding information; and historical human-based determinations on whether the historical reviewed coding information has been reconciled with the historical device-based coding information.

2. The computer-implemented system of claim 1, wherein the processor further transmits the device-based coding information to at least one of a data storage device and a computer-readable-storage medium.

3. The computer-implemented system of claim 1, wherein, during an exercise session, the device-generated information is generated by the electromechanical device.

4. The computer-implemented system of claim 1, wherein the processing of the claim occurs at least one of before, during, and after a healthcare service is rendered.

5. The computer-implemented system of claim 1, wherein the device-generated information comprises at least one of medical result information and medical coding information.

6. The computer-implemented system of claim 1, wherein, using the device-generated information, the processor is further configured to determine device-based exercise result information.

7. The computer-implemented system of claim 6, wherein the processor is further configured to transmit the device-based exercise result information to a notes database.

8. The computer-implemented system of claim 1, wherein the processor is further configured to transmit the device-based coding information to an electronic records database.

9. The computer-implemented system of claim 1, wherein the processor is further configured to:
    receive reviewed coding information from an electronic records database, wherein, using the reviewed coding information and the device-based coding information, the processor is further configured to determine a match indicator; and
    transmit the match indicator to the claim adjudication server.

10. The computer-implemented system of claim 1, wherein the electromechanical device comprises one of a treadmill, an electromechanical spin-wheel, an electromechanical bicycle, an exercise and rehabilitation device, a physical therapy device, or some combination thereof.

11. The computer-implemented system of claim 1, wherein the healthcare services provided during the telemedicine session comprise exercises performed by the user on the electromechanical device during the telemedicine session.

12. The computer-implemented system of claim 1, wherein the one or more machine learning models are further trained to determine, based on the telemedicine information, the healthcare services provided during the telemedicine session, wherein the healthcare services provided during the telemedicine session comprising actions performed by a healthcare provider during the telemedicine session, and wherein the processor is further configured to determine, by using the one or more machine learning models and based on the telemedicine information, the device-based coding information.

13. A system for processing medical claims, comprising:
    an electromechanical device configured to generate device-generated information while a user performs a treatment plan with the electromechanical device;
    a patient interface associated with the electromechanical device and configured to present telemedicine information associated with a telemedicine session;
    one or more processors configured to:
        generate one or more machine learning models trained to determine, based on the device-generated information, the exercises that are performed during the telemedicine session;
        determine, by using the one or more machine learning models and based on the device-generated information, device-based coding information; and
        transmit the device-based coding information to a claim adjuration adjudication server,
    wherein the one or more processors are further configured to generate the one or more machine learning models using training data comprising: historical device-generated information; historical device-based coding information; historical reviewed coding information; historical computer-based determinations on whether the historical reviewed coding information can be reconciled with the historical device-based coding information; and historical human-based determinations on whether the historical reviewed coding information has been reconciled with the historical device-based coding information.

14. The system of claim 13, wherein the processor transmits the device-based coding information to at least one of a data storage device and a computer-readable-storage medium.

15. The system of claim 13, wherein the device-generated information is generated by the electromechanical device.

16. The system of claim 13, wherein the processing of the claim occurs at least one of before, during, and after a healthcare service is rendered.

17. The system of claim 13, wherein the device-generated information comprises at least one of medical result information and medical coding information.

18. The system of claim 13, wherein, using the device-generated information, the processor is further configured to determine device-based exercise result information.

19. The system of claim 18, wherein the processor is further configured to transmit the device-based exercise result information to a notes database.

20. The system of claim 13, wherein the processor is further configured to transmit the device-based coding information to an electronic records database.

21. The system of claim 13, wherein the processor is further configured to:
receive reviewed coding information from an electronic records database, wherein, using the reviewed coding information and the device-based coding information, the processor is further configured to determine a match indicator; and
transmit the match indicator to the claim adjudication server.

22. The system of claim 13, wherein the electromechanical device comprises one of a treadmill, an electromechanical spin-wheel, an electromechanical bicycle, an exercise and rehabilitation device, a physical therapy device, or some combination thereof.

23. A method for operating a clinic server processing a claim for a service, comprising:
receiving device-generated information from an electromechanical device while a user performs a treatment plan with the electromechanical device;
presenting, with a patient interface associated the electromechanical device, telemedicine information associated with a telemedicine session;
generating, with one or more processors, one or more machine learning models trained to determine, based on the device-generated information, exercises that are performed during the telemedicine session;
determining, by using the one or more machine learning models and based on the device-generated information, device-based coding information; and
transmitting the device-based coding information to a claim adjudication server,
wherein generating the one or more machine learning models by the one or more processors includes generating the one or more machine learning models using training data comprising: historical device-generated information; historical device-based coding information; historical reviewed coding information; historical computer-based determinations on whether the historical reviewed coding information can be reconciled with the historical device-based coding information; and historical human-based determinations on whether the historical reviewed coding information has been reconciled with the historical device-based coding information.

24. The method of claim 23, further comprising transmitting the device-based coding information to at least one of a data storage device and a computer-readable-storage medium.

25. The method of claim 23, wherein processing the claim occurs at least one of before, during, and after the service is rendered.

26. The method of claim 23, wherein the electromechanical device comprises one of a treadmill, an electromechanical spin-wheel, an electromechanical bicycle, an exercise and rehabilitation device, a physical therapy device, or some combination thereof.

* * * * *